United States Patent
Clark et al.

(10) Patent No.: US 10,099,243 B2
(45) Date of Patent: Oct. 16, 2018

(54) ADHESIVE DISPENSING DEVICE HAVING OPTIMIZED RESERVOIR AND CAPACITIVE LEVEL SENSOR

(71) Applicant: NORDSON CORPORATION, Westlake, OH (US)

(72) Inventors: Justin A. Clark, Buford, GA (US); Steven Clark, Cumming, GA (US); Peter W. Estelle, Norcross, GA (US); Jeffrey E. Owen, Suwanee, GA (US); Robert J. Woodlief, Suwanee, GA (US); David R. Jeter, Woodstock, GA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 14/991,952

(22) Filed: Jan. 10, 2016

(65) Prior Publication Data

US 2016/0121359 A1   May 5, 2016

Related U.S. Application Data

(62) Division of application No. 13/799,622, filed on Mar. 13, 2013, now Pat. No. 9,304,028.

(Continued)

(51) Int. Cl.
*B05C 11/10* (2006.01)
*G01F 23/26* (2006.01)

(52) U.S. Cl.
CPC .......... *B05C 11/1042* (2013.01); *G01F 23/26* (2013.01); *G01F 23/263* (2013.01); *G01F 23/268* (2013.01)

(58) Field of Classification Search
CPC ... B05C 11/1042; G01F 23/26; G01F 23/263; G01F 23/268
(Continued)

(56) References Cited

U.S. PATENT DOCUMENTS 2,672,215 A   3/1954   Schmid
2,744,792 A   5/1956   Finn et al.
(Continued)

FOREIGN PATENT DOCUMENTS

CN   201102271 Y   8/2008
CN   202116049 U   1/2012
(Continued)

OTHER PUBLICATIONS

European Application No. 15162622.3: Extended European Search Report dated Dec. 2, 2015, 8 pages.
(Continued)

*Primary Examiner* — Benjamin R Shaw
(74) *Attorney, Agent, or Firm* — Baker & Hostetler LLP

(57) ABSTRACT

An adhesive dispensing device includes a heater unit for melting adhesive, a fill system communicating with a receiving space for feeding the heater unit, and a reservoir for receiving melted adhesive from the heater unit. The dispensing device also includes a capacitive level sensor located along a sidewall of the receiving space such that the level of adhesive in the receiving space can be detected by sensing the difference in dielectric capacitance where the adhesive is located compared to where air acts as the dielectric. The size of the driven electrode produces a broader sensing window capable of generating multiple control signals corresponding to different fill levels of adhesive. The receiving space and reservoir are minimized in size so that adhesive is not held at elevated temperatures long enough to char or degrade.

16 Claims, 13 Drawing Sheets

Related U.S. Application Data

(60) Provisional application No. 61/703,454, filed on Sep. 20, 2012.

(58) Field of Classification Search
USPC .......................................................... 222/23
See application file for complete search history.

(56) References Cited

U.S. PATENT DOCUMENTS

| | | | |
|---|---|---|---|
| 2,824,335 A | 2/1958 | Moffat et al. | |
| 2,868,015 A * | 1/1959 | Haropulos | G01F 23/263 361/284 |
| 3,030,153 A | 4/1962 | Krenke et al. | |
| 3,219,394 A * | 11/1965 | Moss | B65G 53/24 406/152 |
| 3,377,861 A * | 4/1968 | Thaler | G01F 23/263 73/304 C |
| 3,580,644 A | 5/1971 | Ballard et al. | |
| 3,756,456 A | 9/1973 | Georgi | |
| 3,773,069 A | 11/1973 | Rebentisch | |
| 3,792,801 A | 2/1974 | Baker et al. | |
| 3,964,645 A * | 6/1976 | Scholl | F04C 13/002 219/421 |
| 3,981,416 A | 9/1976 | Scholl | |
| 4,084,628 A | 4/1978 | Schmid | |
| 4,086,466 A | 4/1978 | Scharlack | |
| 4,277,773 A * | 7/1981 | Blatnik | G01F 23/242 116/109 |
| 4,417,675 A | 11/1983 | Abt et al. | |
| 4,437,581 A * | 3/1984 | Coker | B05B 7/166 222/54 |
| 4,441,450 A | 4/1984 | Dettelbach et al. | |
| 4,474,311 A * | 10/1984 | Petrecca | B29B 13/022 126/343.5 R |
| 4,479,600 A | 10/1984 | Albright | |
| 4,482,367 A | 11/1984 | Howeth | |
| 4,485,941 A * | 12/1984 | Frates | B29B 13/022 222/146.5 |
| 4,485,942 A | 12/1984 | Petrecca | |
| 4,583,885 A | 4/1986 | Thiele | |
| 4,613,059 A | 9/1986 | Merkel | |
| 4,641,764 A | 2/1987 | Faulkner, III | |
| 4,688,432 A * | 8/1987 | Marsh | G01F 1/58 73/861.15 |
| 4,785,996 A | 11/1988 | Ziecker et al. | |
| 4,821,922 A | 4/1989 | Miller et al. | |
| 4,850,425 A | 7/1989 | Anderson | |
| 4,898,527 A | 2/1990 | Claassen | |
| 4,994,984 A | 2/1991 | Massimo | |
| 5,006,018 A | 4/1991 | Depew | |
| 5,174,472 A | 12/1992 | Raque et al. | |
| 5,287,086 A * | 2/1994 | Gibb | F04B 23/021 324/660 |
| 5,294,218 A | 3/1994 | Fiorentini et al. | |
| 5,332,366 A | 7/1994 | Anderson | |
| 5,347,867 A * | 9/1994 | Pangerl | G01P 15/125 29/25.41 |
| 5,589,203 A | 12/1996 | Sato | |
| 5,680,961 A * | 10/1997 | Boccagno | B05C 11/1042 219/421 |
| 5,680,963 A * | 10/1997 | Brusko | B05C 11/1042 222/146.5 |
| 5,699,938 A * | 12/1997 | Siddiqui | B05C 11/1042 219/421 |
| 5,706,982 A * | 1/1998 | Siddiqui | B29B 13/022 210/108 |
| 5,715,972 A | 2/1998 | Siddiqui | |
| 5,747,689 A * | 5/1998 | Hampo | G01F 23/265 702/55 |
| 5,791,830 A | 8/1998 | Fort et al. | |
| 5,909,829 A | 6/1999 | Wegman et al. | |
| 5,927,555 A | 7/1999 | Harben et al. | |
| 6,039,513 A | 3/2000 | Law | |
| 6,073,488 A * | 6/2000 | Byatt | G01B 7/085 73/290 R |
| 6,095,803 A | 8/2000 | Slater | |
| 6,175,101 B1 | 1/2001 | Miller et al. | |
| 6,230,936 B1 | 5/2001 | Lasko | |
| 6,318,599 B2 | 11/2001 | Estelle et al. | |
| 6,352,173 B1 | 3/2002 | Duckworth | |
| 6,380,861 B2 | 4/2002 | Estelle et al. | |
| 6,471,751 B1 | 10/2002 | Semanderes et al. | |
| 6,616,721 B2 | 9/2003 | Oh | |
| 6,883,684 B2 * | 4/2005 | Jeter | B05C 11/1042 222/146.2 |
| 7,263,781 B2 | 9/2007 | Sielemann | |
| 7,626,143 B2 * | 12/2009 | Miller | B05C 5/001 219/421 |
| 8,157,483 B2 | 4/2012 | Volkmann | |
| 8,201,717 B2 | 6/2012 | Varga et al. | |
| 8,383,991 B2 | 2/2013 | Ganzer et al. | |
| 8,430,230 B1 | 4/2013 | Ferguson et al. | |
| 8,580,006 B2 | 11/2013 | LaCroix et al. | |
| 9,427,766 B2 | 8/2016 | Varga | |
| 2001/0023880 A1 | 9/2001 | Estelle et al. | |
| 2002/0079325 A1 | 6/2002 | Estelle | |
| 2003/0021700 A1 | 1/2003 | Serafin et al. | |
| 2003/0080154 A1 | 5/2003 | Jeter | |
| 2003/0080155 A1 * | 5/2003 | Jeter | B29B 13/022 222/146.5 |
| 2003/0080156 A1 | 5/2003 | Jeter et al. | |
| 2004/0055739 A1 | 3/2004 | Suckow et al. | |
| 2004/0167738 A1 | 8/2004 | Miller | |
| 2005/0095359 A1 | 5/2005 | Pallante et al. | |
| 2005/0274740 A1 * | 12/2005 | Duckworth | B05C 11/1042 222/146.5 |
| 2006/0055503 A1 * | 3/2006 | Tanida | G01N 27/225 338/38 |
| 2006/0159565 A1 | 7/2006 | Sanwald | |
| 2006/0289560 A1 | 12/2006 | Bourget et al. | |
| 2007/0080157 A1 | 4/2007 | Mehaffy et al. | |
| 2007/0216424 A1 * | 9/2007 | Sieh | G01F 23/268 324/662 |
| 2008/0000928 A1 * | 1/2008 | Choiniere | B05B 9/007 222/94 |
| 2008/0095637 A1 * | 4/2008 | Burdi | F04D 15/0218 417/36 |
| 2008/0120046 A1 * | 5/2008 | Tung | G01F 23/263 702/52 |
| 2008/0145248 A1 | 6/2008 | Kato et al. | |
| 2008/0156801 A1 * | 7/2008 | Tung | G01F 23/242 220/200 |
| 2008/0196512 A1 | 8/2008 | Miller | |
| 2008/0199323 A1 | 8/2008 | Bauck et al. | |
| 2008/0206066 A1 | 8/2008 | Nguyen et al. | |
| 2008/0282795 A1 * | 11/2008 | Zabel | G01F 23/268 73/304 C |
| 2008/0302477 A1 | 12/2008 | Varga et al. | |
| 2009/0229359 A1 * | 9/2009 | Reimelt | G01F 23/284 73/304 R |
| 2009/0229683 A1 * | 9/2009 | Baek | G01F 23/263 137/386 |
| 2009/0285983 A1 | 11/2009 | Baldauf et al. | |
| 2010/0282088 A1 | 11/2010 | Deuber et al. | |
| 2011/0000309 A1 * | 1/2011 | Griffiths | A61B 5/204 73/861.08 |
| 2011/0002793 A1 | 1/2011 | Bauck et al. | |
| 2011/0042408 A1 | 2/2011 | Giordano et al. | |
| 2011/0079078 A1 * | 4/2011 | Ho | G01F 23/268 73/304 C |
| 2011/0100120 A1 * | 5/2011 | Neuburger | G01F 23/2845 73/304 R |
| 2011/0259919 A1 | 10/2011 | Choiniere et al. | |
| 2012/0051945 A1 | 3/2012 | Orndorff et al. | |
| 2012/0223094 A1 | 9/2012 | Rickard, Jr. et al. | |
| 2012/0227484 A1 * | 9/2012 | Chen | A61M 1/28 73/304 R |
| 2012/0247665 A1 | 10/2012 | Varga et al. | |
| 2012/0273071 A1 | 11/2012 | Kai | |
| 2013/0105003 A1 | 5/2013 | Quam et al. | |
| 2013/0105004 A1 | 5/2013 | Tix et al. | |

(56) References Cited

U.S. PATENT DOCUMENTS

| | | | |
|---|---|---|---|
| 2013/0105005 A1 | 5/2013 | Tix et al. | |
| 2013/0105039 A1 | 5/2013 | Tix et al. | |
| 2013/0105517 A1 | 5/2013 | Tix et al. | |
| 2013/0105526 A1 | 5/2013 | Ross et al. | |
| 2013/0112279 A1 | 5/2013 | Ross et al. | |
| 2013/0112280 A1 | 5/2013 | Quam et al. | |
| 2013/0112294 A1 | 5/2013 | Ross et al. | |
| 2013/0112312 A1 | 5/2013 | Ross et al. | |
| 2013/0112709 A1 | 5/2013 | Ross et al. | |
| 2013/0112710 A1 | 5/2013 | Ross et al. | |
| 2013/0112711 A1 | 5/2013 | Lind et al. | |
| 2013/0115016 A1 | 5/2013 | Ross et al. | |
| 2013/0205893 A1* | 8/2013 | Shearer | G01F 23/268 73/290 R |
| 2014/0014683 A1* | 1/2014 | Owen | B05C 5/027 222/54 |
| 2014/0020463 A1* | 1/2014 | Ikeya | G01F 23/263 73/304 C |
| 2014/0203040 A1 | 7/2014 | Clark et al. | |
| 2016/0279662 A1 | 9/2016 | Reuter | |

FOREIGN PATENT DOCUMENTS

| | | | |
|---|---|---|---|
| DE | 3815089 | A1 | 11/1989 |
| DE | 19923410 | A1 | 11/1999 |
| DE | 10156691 | A1 | 5/2003 |
| EP | 0072679 | A1 | 2/1983 |
| EP | 1350743 | A1 | 10/2003 |
| EP | 2119509 | A2 | 11/2009 |
| EP | 3108968 | A1 | 12/2016 |
| FR | 1366936 | A | 7/1964 |
| FR | 2787770 | A1 | 6/2000 |
| GB | 1562562 | A | 3/1980 |
| GB | 2485041 | A | 5/2012 |
| JP | 2009-523634 | A | 6/2009 |
| JP | 2015-202495 | A | 11/2015 |
| JP | 2016-188852 | A | 11/2016 |
| WO | 98/14314 | A1 | 4/1998 |
| WO | 2007/084891 | A2 | 7/2007 |
| WO | 2009046545 | A1 | 4/2009 |
| WO | 2012095838 | A1 | 7/2012 |

OTHER PUBLICATIONS

U.S. Appl. No. 13/799,788: Non-Final Office Action dated Jun. 12, 2014, 24 pages.
European Patent Application No. 13184144.7: European Search Report dated Mar. 25, 2014, 6 pages.
European Patent Application No. 13187639.3: Extended European Search Report dated Feb. 28, 2014, 5 pages.
European Patent Application No. 13185184: Extended European Search Report dated Jun. 6, 2014.
Japan Patent Application No. 2013-194839; Reasons for Refusal; dated Apr. 13, 2017; 7 pages.
Meltex GmbH; Product Information Sheet; Hot Melt Applicator MX 2003, 29/120b/3000/05'89/BU e (Undated) (2 pages).
Meltex GmbH; Product Information Sheet; Hot Melt Applicator MX 2001, 29/119b/3000/05'89/BU e (Undated) (2 pages).
Meltex Corporation; Product Information Sheet; Hot Melt Applicator MP 400; (Undated) (1 page).
Fluid-Air Products Inc., InvisiPac, (Jan. 5, 2013) (12 pages).
European Search Report dated Dec. 2, 2015.
European Patent Office, Extended European Search Report in EP Patent Application No. 13185893.8, dated Apr. 1, 2015 (6 pages).
Chinese Patent Application No. 201310432540.2; Office Action; dated Aug. 8, 2017; 8 pages.

\* cited by examiner

ADHESIVE DISPENSING DEVICE HAVING OPTIMIZED RESERVOIR AND CAPACITIVE LEVEL SENSOR

CROSS-REFERENCE TO RELATED APPLICATIONS

This application is a divisional of U.S. patent application Ser. No. 13/799,622, filed Mar. 13, 2013, which claims the benefit of U.S. Provisional Patent Application No. 61/703,454, filed on Sep. 20, 2012, the disclosures of which are incorporated by reference herein in their entirety.

FIELD OF THE INVENTION

The present invention generally relates to an adhesive dispenser, and more particularly, to components of a melt subassembly configured to heat adhesive prior to dispensing.

BACKGROUND

A conventional dispensing device for supplying heated adhesive (i.e., a hot-melt adhesive dispensing device) generally includes an inlet for receiving adhesive materials in solid or liquid form, a heater grid in communication with the inlet for heating the adhesive materials, an outlet in communication with the heater grid for receiving the heated adhesive from the heated grid, and a pump in communication with the heater grid and the outlet for driving and controlling the dispensation of the heated adhesive through the outlet. One or more hoses may also be connected to the outlet to direct the dispensation of heated adhesive to adhesive dispensing guns or modules located downstream from the dispensing device. Furthermore, conventional dispensing devices generally include a controller (e.g., a processor and a memory) and input controls electrically connected to the controller to provide a user interface with the dispensing device. The controller is in communication with the pump, heater grid, and/or other components of the device, such that the controller controls the dispensation of the heated adhesive.

Conventional hot-melt adhesive dispensing devices typically operate at ranges of temperatures sufficient to melt the received adhesive and heat the adhesive to an elevated application temperature prior to dispensing the heated adhesive. In order to ensure that the demand for heated adhesive from the downstream gun(s) and module(s) is satisfied, the adhesive dispensing devices are designed with the capability to generate a predetermined maximum flow of molten adhesive. As throughput requirements increase (e.g., up to 20 lb/hour or more), adhesive dispensing devices have traditionally increased the size of the heater grid and the size of the hopper and reservoir associated with the heater grid in order to ensure that the maximum flow of molten adhesive can be supplied.

However, large hoppers and reservoirs result in a large amount of hot-melt adhesive being held at the elevated application temperature within the adhesive dispensing device. This holding of the hot-melt adhesive at the elevated application temperature may keep the hot-melt adhesive at high temperature for only about 1 to 2 hours during maximum flow, but most conventional adhesive dispensing devices do not operate continuously at the maximum flow. To this end, all adhesive dispensing devices operate with long periods of time where the production line is not in use and the demand for molten adhesive is zero, or lower than the maximum flow. During these periods of operation, large amounts of hot-melt adhesive may be held at the elevated application temperature for long periods of time, which can lead to degradation and/or charring of the adhesive, negative effects on the bonding characteristics of the adhesive, clogging of the adhesive dispensing device, and/or additional system downtime.

In addition, the supply of adhesive material into the hopper must also be monitored to maintain a generally consistent level of hot-melt adhesive in the adhesive dispensing device. Adhesive, generally in the form of small shaped pellets, is delivered to the hopper by various methods, including manual filling and automated filling. In one known method of filling the hopper, adhesive pellets are moved into the hopper with pressurized air that flows at a relatively high rate of speed. In order to monitor the level of hot-melt adhesive in the hopper, the hopper may include a level sensor in the form of a probe or some other structure extending into the middle of the hopper to detect the amount of adhesive material located in the hopper. As the adhesive pellets are delivered into the hopper by various methods, the probe may collect adhesive material that sticks on or splashes onto the probe. This collection of adhesive material, if not rapidly removed, may adversely affect the accuracy of readings from the level sensor. However, it has proven difficult to remove this collection of adhesive material from probe-like level sensors during operation. Thus, in circumstances of high throughput through the adhesive dispensing device, a lag in accurate readings from the level sensor could lead to insufficient or excessive levels of adhesive material within the hopper.

For reasons such as these, an improved hot-melt adhesive dispenser device and level sensor would be desirable for use with different types of hoppers and different types of filling processes.

SUMMARY OF THE INVENTION

According to one embodiment of the invention, a fluid level sensor is configured to measure a fill level of a hot melt adhesive within a receiving space at least partially defined by a sidewall and configured to receive adhesive to be melted. The level sensor includes a plate element having an electrically driven electrode and a ground electrode operatively connected for measuring a dielectric capacitance of air and adhesive acting as a dielectric between the driven and ground electrodes. The ground electrode is electrically connected to the sidewall such that the sidewall forms at least a portion of the ground electrode. The level sensor also includes at least one fastener mount connected to the plate element. The fastener mount is adapted to receive a fastener that couples the plate element into adjacent relationship with the sidewall. As a result, the dielectric capacitance measured by the plate element varies with the fill level of the adhesive in the receiving space.

In one aspect, the plate element is a printed circuit board. In another aspect, the plate element is sized to engage a majority of the sidewall such that heat energy conducted through the sidewall is transferred to the plate element. This heat energy rapidly melts off any adhesive residue on the plate element above the fill level of the adhesive. Consequently, localized effects such as adhesive pellets sticking onto the plate element have minimal effect on the readings of fill level, unlike probe-like level sensors that may be affected for long periods of time by the sticking of adhesive pellets to the level sensor. Therefore, the plate element may be mounted flush with the sidewall. Additionally, a gasket may be located between the sidewall and the plate element to prevent adhesive from flowing between the sidewall and the plate element.

In another aspect, the driven electrode defines a plate surface area and the sidewall defines a sidewall surface area. The size of the driven electrode and the plate surface area relative to the sidewall surface area is maximized to provide a broader sensing window. The broader sensing window is capable of generating multiple control signals corresponding to different fill levels of adhesive. In one example, the ratio of the plate surface area to the sidewall surface area is higher than 0.4 to 1. However, the ratio between these surface areas may be modified in other embodiments as long as the broader sensing window is maintained by the size of the plate element and the driven electrode.

In another aspect, the plate element includes a front face that faces towards the adhesive in the receiving space. The front face includes an inner portion separated from an outer portion by an electric barrier. The inner portion operates as the driven electrode described above. In some embodiments, the outer portion of the front face operates as the ground electrode. In other embodiments, the receiving space is also partially defined by an opposite sidewall facing towards the plate element, and the outer portion of the front face operates as an electrically driven shield. This driven shield forces the level sensor to measure the dielectric capacitance of air and adhesive located between the driven electrode and the opposite sidewall.

The fluid level sensor measurements of dielectric capacitance are also affected by the temperature of the level sensor, which varies as a result of cold pressurized air and unmelted adhesive periodically entering the receiving space. In order to compensate for this, the fluid level sensor may also include a timer operatively coupled to the plate element and to a controller, and a control subroutine loaded onto the controller. The controller operates to receive the dielectric capacitance measurements and uses those measurements to control when a fill system is actuated to provide more unmelted adhesive to the receiving space. The control subroutine automatically compensates for temperature changes at the level sensor by estimating the temperature changes at the plate element based on a time measured by the timer since a most recent actuation of the fill system. As a result, the additional expense and maintenance associated with adding another temperature sensor at the level sensor is avoided.

According to another embodiment of the invention, a fluid level sensor is configured to measure a fill level of a hot melt adhesive within a receiving space at least partially defined by a sidewall. The level sensor includes a plate element having a printed circuit board. The level sensor also includes an electrically driven electrode and a ground electrode located on the printed circuit board and operatively connected for measuring a dielectric capacitance of air and adhesive acting as a dielectric between the driven and ground electrodes. The ground electrode may be electrically connected to the sidewall such that the sidewall forms at least a portion of the ground electrode. The plate element is positioned such that the dielectric capacitance measured by the plate element varies with the fill level of the adhesive.

In yet another embodiment according to the invention, a fluid level sensor is configured to measure a fill level of a hot melt adhesive within a receiving space at least partially defined by a sidewall having a sidewall surface area. The level sensor includes a plate element. The level sensor also includes an electrically driven electrode located on the plate element and defining a plate surface area. The level sensor further includes a ground electrode located on the plate element and operatively connected to the driven electrode for measuring a dielectric capacitance of air and adhesive acting as a dielectric between the driven and ground electrodes. The ground electrode may be electrically connected to the sidewall such that the sidewall forms at least a portion of the ground electrode. The plate element is positioned such that the dielectric capacitance measured by the plate element varies with the fill level of the adhesive. Moreover, the size of the driven electrode and the plate surface area relative to the sidewall surface area is maximized to provide a broader sensing window. The broader sensing window is capable of generating multiple control signals corresponding to different fill levels of adhesive within the receiving space.

According to another embodiment of the invention, a melt subassembly is configured to receive and melt a hot melt adhesive. The melt subassembly includes a sidewall at least partially enclosing a receiving space for receiving unmelted adhesive. A heater unit is positioned to receive the adhesive from the receiving space and then heat and melt the adhesive. The melt subassembly also includes a fluid level sensor for measuring a fill level of the adhesive within the receiving space. The level sensor includes a plate element having an electrically driven electrode and a ground electrode operatively connected for measuring a dielectric capacitance of air and adhesive acting as a dielectric between the driven and ground electrodes. The ground electrode may be electrically connected to the sidewall such that the sidewall forms at least a portion of the ground electrode. The level sensor also includes at least one fastener mount connected to the plate element. The fastener mount is adapted to receive a fastener that couples the plate element into adjacent relationship with the sidewall. As a result, the dielectric capacitance measured by the plate element varies with the fill level of the adhesive.

In still another embodiment according to the invention, an adhesive dispensing device is configured to receive unmelted adhesive, melt and heat the adhesive, and then deliver the melted adhesive for dispensing. To this end, the adhesive dispensing device includes a heater unit adapted to heat and melt an adhesive to an elevated application temperature, a receiving space defined at least partially by a sidewall and positioned to feed the adhesive through the heater unit, and a reservoir positioned to receive the adhesive from the heater unit. The receiving space and the reservoir define a collective storage volume that is minimized such that the adhesive is not held at the elevated application temperature long enough to degrade or char during periods of low adhesive flow. The adhesive dispensing device also includes a pump for directing the adhesive out of the reservoir, and a level sensor for measuring a fill level of the adhesive within the receiving space. The level sensor includes a plate element having an electrically driven electrode and a ground electrode operatively connected for measuring a dielectric capacitance of air and adhesive acting as a dielectric between the driven and ground electrodes. The ground electrode may be electrically connected to the sidewall such that the sidewall forms at least a portion of the ground electrode. The level sensor is coupled into adjacent relationship with the sidewall such that the dielectric capacitance measured by the plate element varies with the fill level of the adhesive. This measurement enables the rapid delivery of additional adhesive to the receiving space following removal of adhesive from the reservoir to avoid emptying the heater unit and the reservoir during periods of high adhesive flow.

In one aspect, the collective volume of the receiving space and the reservoir is less than two liters. However, the level sensor is responsive enough to changes in the fill level of adhesive to prevent the receiving space and the heater unit from becoming depleted during periods of high throughput despite the relatively small retained volume of adhesive in the adhesive dispensing device. The adhesive dispensing device may further include a cyclonic separator unit configured to receive pellets of adhesive material in an air flow and reduce the velocity of the air flow and the pellets of adhesive before deposit into the receiving space. The pellets of adhesive define a pellet shape that is optimized to enable reliable flow of small amounts of adhesive material to refill the receiving space in a controlled manner. The pellet shape is also optimized to enclose a minimal amount of air when the adhesive is stacked such that the level of adhesive within the receiving space is accurately detected by the level sensor.

In one embodiment, the invention includes a method for melting and delivering a hot melt adhesive from a melt subassembly. The method includes supplying unmelted adhesive from a fill system into a receiving space defined at least partially by a sidewall. The adhesive is heated and melted to an elevated application temperature with a heater unit communicating with the receiving space. The melted adhesive is then pumped out of the melt subassembly for dispensing at a dispensing device. A level sensor senses a fill level of adhesive remaining in the receiving space. The level sensor includes a plate element with an electrically driven electrode and a ground electrode operatively connected for measuring a dielectric capacitance of air and adhesive within the receiving space. Similar to other embodiments, the level sensor is positioned adjacent to the sidewall such that the dielectric capacitance varies with the fill level of the adhesive. The method also includes actuating a new supply of unmelted adhesive from the fill system whenever the fill level of adhesive drops below a refill threshold.

Because the measured dielectric capacitance is affected by changes in temperature at the level sensor, the method may also include compensating the measured dielectric capacitance with a current offset for changes in temperature at the level sensor. The current offset is a function of time elapsed since a most recent supply of unmelted adhesive from the fill system. For example, this compensating includes retrieving an initial offset applied to the temperature of the level sensor along with an adjustment curve known for different temperatures of the level sensor. The time elapsed since the most recent supply of adhesive from the system is measured, and the current offset is calculated based on the initial offset and the time elapsed since the most recent supply of adhesive. The measured dielectric capacitance is then adjusted using the adjustment curve and the current offset, thereby adjusting the fill level measurement determined from this dielectric capacitance.

In one aspect, the actuation of a new supply of unmelted adhesive includes retrieving the current offset applied to the temperature of the level sensor, as calculated above. If the current offset is equal to zero, then the initial offset is set equal to a first predetermined value, while if the current offset is not equal to zero, the initial offset is set equal to the current offset, plus a second predetermined value. To this end, the offset is cumulative over time if the refills of the receiving space occur more frequently. The calculation of the current offset may be performed by retrieving a decay slope for the current offset and then subtracting a product of this decay slope and the elapsed time from the initial offset to determine the current offset. The decay slope may be set to two different values depending on whether the most recent supply of adhesive was stopped by a maximum threshold cycle time for refilling being exceeded. In this regard, a higher decay slope may be applied when the fill cycle time reaches a maximum threshold cycle time because this indicates that the level sensor may not be completely covered with cold adhesive. However, alternative methods of estimating a temperature difference at the level sensor and compensating the corresponding capacitance readings may be used in other embodiments.

In another embodiment according to the invention, an adhesive dispensing device includes a melt subassembly and a control subassembly. The melt subassembly includes a heater unit adapted to melt and heat an adhesive to an elevated application temperature, a receiving space positioned to feed the adhesive through the heater unit, a reservoir for receiving the melted adhesive from the heater unit, and a pump for directing the adhesive from the reservoir to an outlet. The receiving space and the reservoir define a collective storage volume, and the heater unit defines a surface area in contact with the adhesive. The control subassembly includes a controller configured to operate the pump and the heater unit to dispense adhesive material through the outlet. A relation of the collective storage volume of the receiving space and the reservoir to the surface area of the heater unit is minimized such that the adhesive material is not held at the elevated application temperature long enough to degrade or char during periods of low adhesive flow. The adhesive material is also heated rapidly enough to be dispensed at a maximum flow rate during periods of high adhesive flow.

In one aspect, the relation of the collective storage volume to the surface area of the heater unit is less than 1 cubic inch of volume to 1 square inch of surface area. More particularly, the relation of the collective storage volume to the surface area of the heater unit is about 0.7 cubic inches of volume to 1 square inch of surface area. Consequently, the collective volume of the receiving space and the reservoir may be relatively small, such as about two liters. However, the maximum flow rate of adhesive can still be delivered when necessary despite the lowered amount of retained adhesive within the adhesive dispensing device.

These and other objects and advantages of the invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE ILLUSTRATIVE EMBODIMENTS

Figure 1:
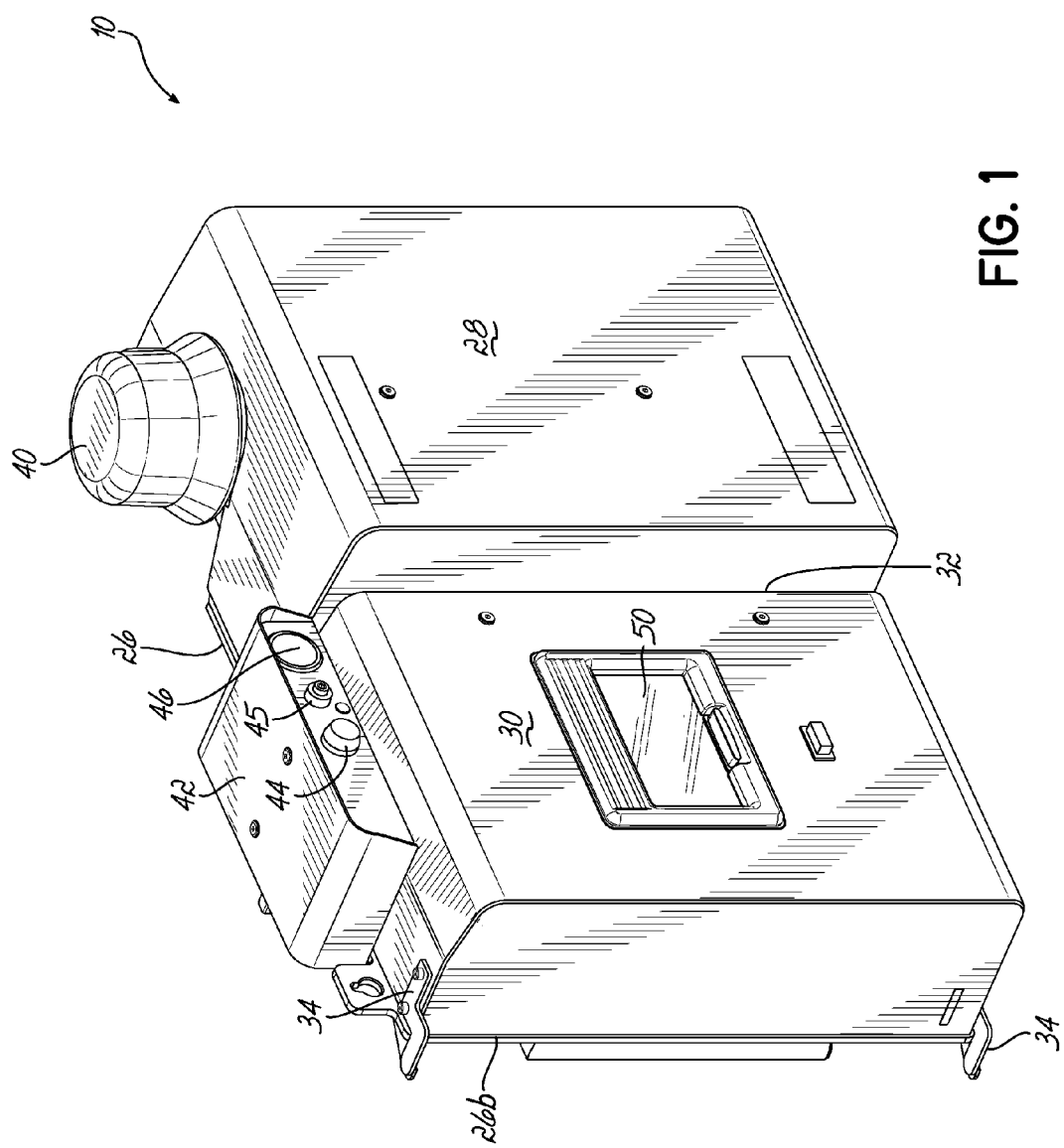
FIG. 1 is a perspective view of an adhesive dispensing device according to one embodiment of the current invention, with a subassembly cover closed.
Figure 2:
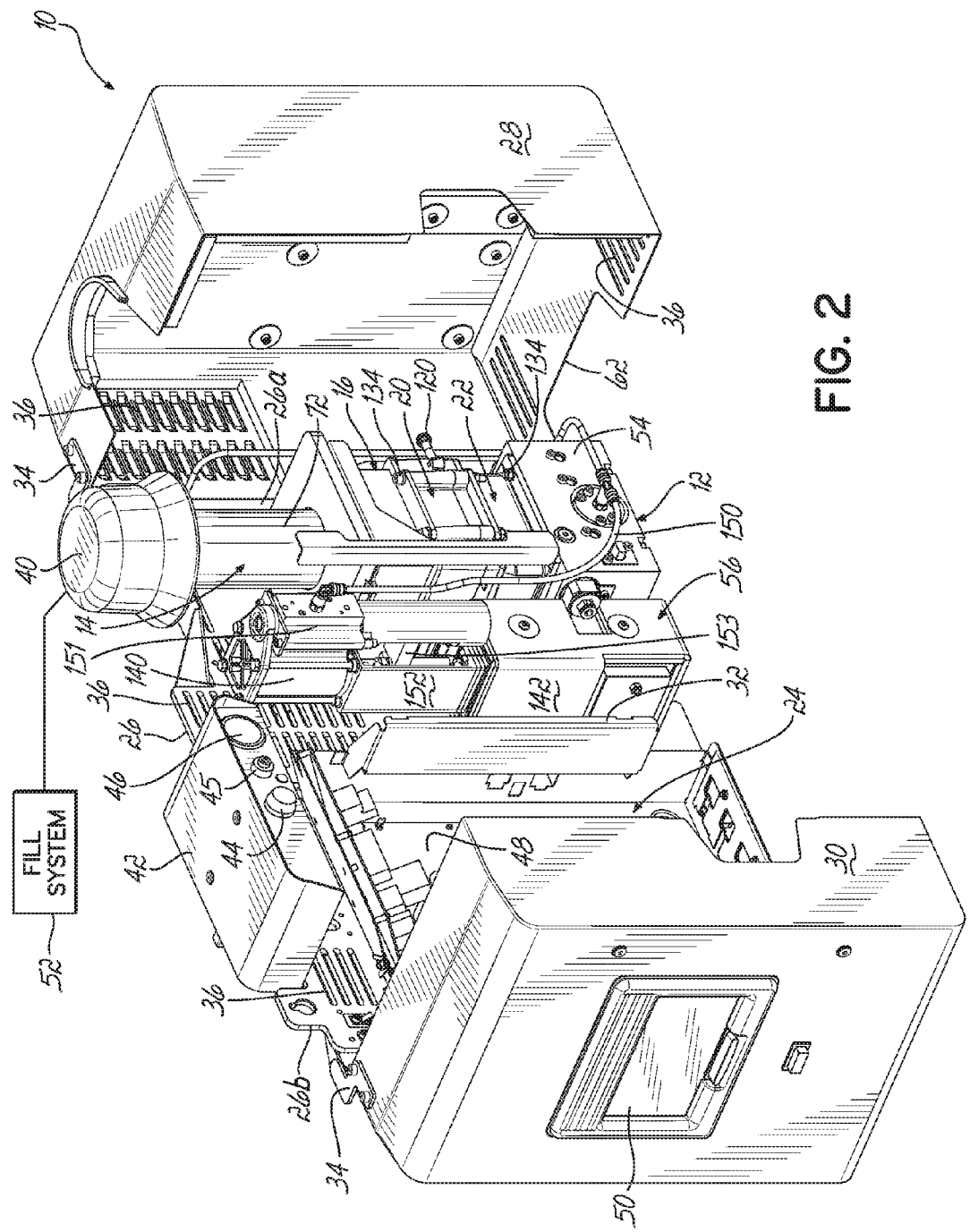
FIG. 2 is a perspective view of the adhesive dispensing device of FIG. 1, with the subassembly cover opened to reveal a melt subassembly.
Figure 3:
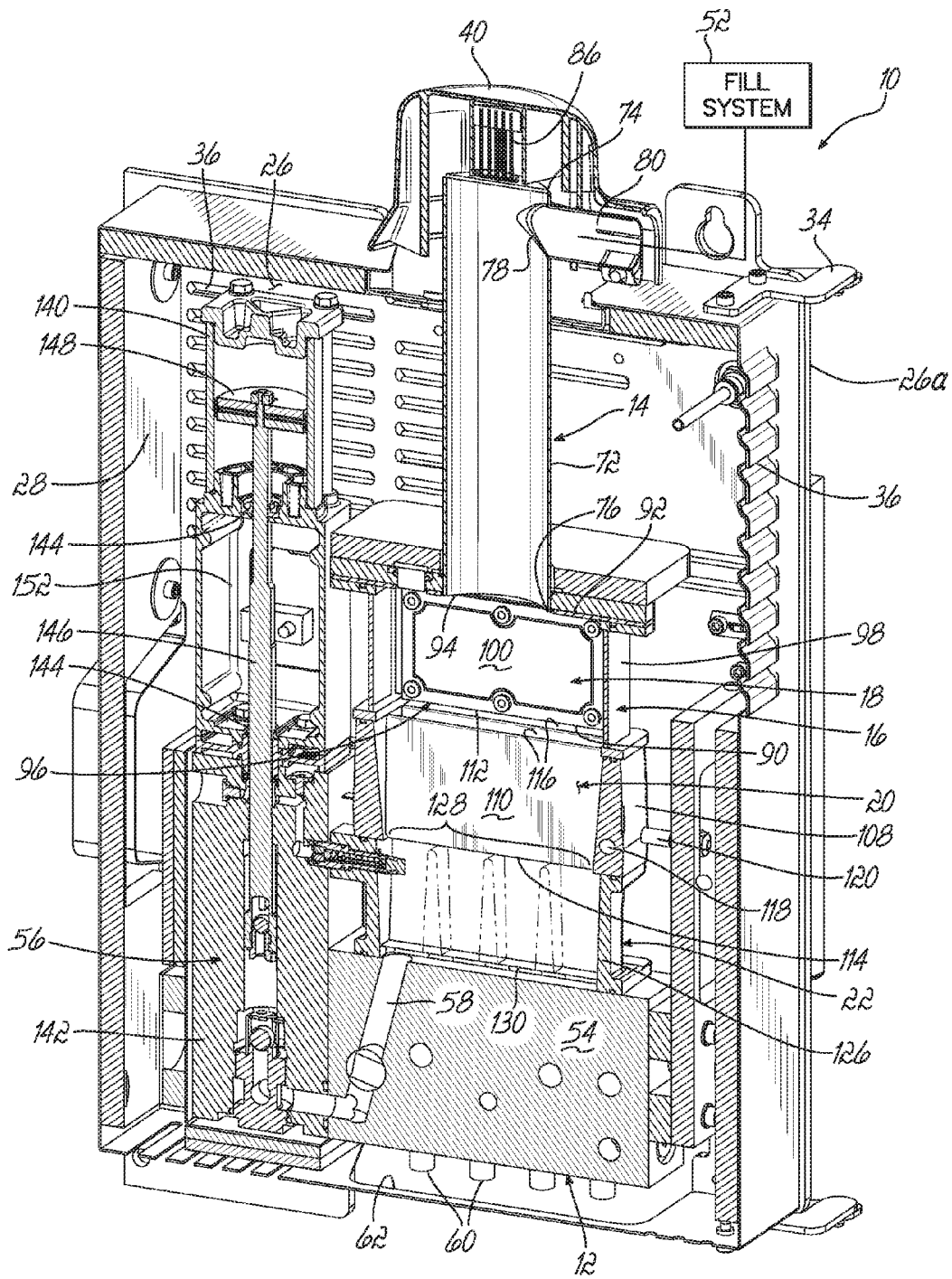
FIG. 3 is a cross-sectional perspective view of at least a portion of adhesive dispensing device of FIG. 2, specifically showing internal features of the melt subassembly.

Referring to FIGS. 1 through 3, an adhesive dispensing device 10 in accordance with one embodiment of the invention is optimized to retain a significantly smaller amount of adhesive material at an elevated application temperature than conventional designs while providing the same maximum flow rate when necessary. More specifically, the adhesive dispensing device 10 includes a melt subassembly 12 that may include a cyclonic separator unit 14, a receiving space 16 with a level sensor 18, a heater unit 20, and a reservoir 22. Each of these elements is described in further detail below. The combination of these elements enables a maximum flow with approximately 80% less retained volume of molten adhesive material held at the elevated application temperature when compared to conventional designs.

The adhesive dispensing device 10 shown in FIGS. 1 through 3 is mounted along a wall surface, as described in U.S. patent application Ser. No. 13/659,291 to Jeter (entitled "Mountable Device For Dispensing Heated Adhesive"), which is co-owned by the assignee of the current application and the disclosure of which is hereby incorporated by reference herein in its entirety. However, it will be understood that the adhesive dispensing device 10 of the invention may be mounted and oriented in any manner without departing from the scope of the invention.

Referring to FIGS. 1 and 2, the adhesive dispensing device 10 includes the melt subassembly 12 and a control subassembly 24, both mounted along a common mounting plate 26. The mounting plate 26 is configured to be coupled to a support wall or structure in a generally vertical orientation as shown. The melt subassembly 12 is mounted adjacent a first terminal end 26a of the mounting plate 26, while the control subassembly 24 is mounted adjacent a second terminal end 26b of the mounting plate 26. In this regard, the melt subassembly 12 is spaced from the control subassembly 24 such that the control subassembly 24 may be isolated from the high operating temperatures (up to 350° F.) of the melt subassembly 12.

The adhesive dispensing device 10 also includes first and second subassembly covers 28, 30 configured to provide selective access to the melt subassembly 12 and to the control subassembly 24, respectively. As shown in the closed position of FIG. 1, the first subassembly cover 28 is coupled to the mounting plate 26 adjacent the first terminal end 26a and is operable to at least partially insulate the melt subassembly 12 from the surrounding environment. The second subassembly cover 30 is coupled to the mounting plate 26 adjacent the second terminal end 26b and is operable to insulate the control subassembly 24 from the melt subassembly 12 and also from the surrounding environment. When the first and second subassembly covers 28, 30 are closed, a thermal gap 32 is formed between the subassembly covers 28, 30 and therefore also between the melt subassembly 12 and the control subassembly 24. This thermal gap 32 further ensures the isolation of the control subassembly 24 from the elevated operating temperatures at the melt subassembly 12.

Each of the first and second subassembly covers 28, 30 is pivotally coupled to the mounting plate 26 at hinge members 34 as shown in FIG. 2. Also shown in FIG. 2, the first subassembly cover 28 includes vents 36 that may be used to avoid overheating of the components of the melt subassembly 12 held within the first subassembly cover 28. However, none of these vents 36 are located towards the thermal gap 32 when the first subassembly cover 28 is closed. The second subassembly cover 30 may also include vents (not shown) facing away from the thermal gap 32 in a similar manner. The mounting plate 26 also includes vents 36 positioned around the melt subassembly 12 and around the control subassembly 24 in the illustrated embodiment. When the first and second subassembly covers 28, 30 are opened as shown in FIG. 2, an operator has access to the components of the melt subassembly 12 and the control subassembly 24 such as when those components need to be repaired. In some embodiments, the melt subassembly 12 may also be pivotally mounted on lift-off hinges (not shown) coupled to the mounting plate 26 so that the melt subassembly 12 can also be pivoted as a unit away from the mounting plate 26 to provide access to the back sides of components of the melt subassembly 12 (for example, to provide access to the connections for the level sensor 18 at the receiving space 16). This pivotal coupling of the melt subassembly 12 may be modified in other embodiments without departing from the scope of the invention.

With continued reference to FIGS. 1 and 2, the first subassembly cover 28 substantially encloses the entire melt assembly 12 in the closed position, except for a top end of the cyclone separator unit 14. This top end (hidden in FIGS. 1 and 2) is covered by a protective cap 40 that insulates the typically metal material forming the cyclone separator unit 14 from an operator who may be working with the adhesive dispensing device 10 when the first subassembly cover 28 is closed. Similarly, the second subassembly cover 30 substantially encloses the entire control subassembly 24 except for an external controller box 42 that may include several elements used for various purposes during operation of the adhesive dispensing device 10. For example, the controller box 42 in the exemplary embodiment includes a siren 44, a screw 45 used to adjust air pressure in a pump described below, and a pressure gage 46 for measuring this air pressure. All other components of the melt subassembly 12 and the control subassembly 24 are isolated from direct contact with an operator during operation of the adhesive dispensing device 10.

The control subassembly 24 is shown in further detail in FIGS. 1 and 2. To this end, the control subassembly 24 includes a controller 48 (e.g., one or more integrated circuits) operatively connected to a control interface 50. The controller 48 is operable to communicate with, and control the actuation of components of the melt subassembly 12. For example, the controller may receive signals from the level sensor 18 and cause actuation of more adhesive pellets to be supplied from a fill system 52 (shown schematically in FIGS. 2 and 4) via the cyclonic separator unit 14 when necessary. The control interface 50 is mounted on the second subassembly cover 30 and is operatively connected to the controller 48, such that an operator of the adhesive dispensing device 10 may receive information from the controller 48 or provide input data to the controller 48 at the control interface 50. Although the control interface 50 is illustrated as a display screen in the illustrated embodiment, it will be understood that touch screen displays, keypads, keyboards, and other known input/output devices may be incorporated into the control interface 50. The control subassembly 24 also includes the controller box 42 previously described, and this controller box 42 is operatively connected to the controller 48 to provide additional input/output capabilities between the operator and the controller 48. The control subassembly 24 may also include a timer 53 (shown schematically in FIG. 5 connected to the controller 48 for measuring various time variables used in estimating a temperature of the level sensor 18 and in compensating fill level readings from the level sensor 18, as described in detail with reference to FIGS. 12 through 15 below.

The melt subassembly 12 is shown in further detail with reference to FIGS. 2 through 5. As briefly described above, the melt subassembly 12 includes a plurality of components that are configured to receive pellets of adhesive material from the fill system 52, melt and heat those pellets into molten adhesive at an elevated application temperature, and dispense the molten adhesive from outlets to be delivered to downstream guns or modules (not shown). As shown in FIG. 2, the cyclonic separator unit 14 is mounted on top of a hopper 16 defining the receiving space 16 in this exemplary embodiment and is separated from the reservoir 22 by the heater unit 20 and the receiving space 16. Thus, a generally gravity-driven flow of adhesive is caused from the cyclonic separator unit 14 to the heater unit 20 for melting, and then from the heater unit 20 into the reservoir 22. The melt subassembly 12 also includes a manifold 54 located below the reservoir 22 and a pump 56 disposed alongside the other components within the space defined by the mounting plate 26 and the first subassembly cover 28. The manifold 54 includes various conduits 58 extending between the reservoir 22, the pump 56, and one or more outlets 60 located at the bottom of the melt subassembly 12. The pump 56 operates to actuate movement of molten adhesive from the reservoir 22 and through the outlets 60 when required. The outlets 60 may extend through a cutout 62 at the bottom of the first subassembly cover 28 for connection to heated hoses or other conveyance elements for delivering the molten adhesive to downstream guns or modules (not shown).

The cyclonic separator unit 14 receives adhesive pellets driven by a pressurized air flow through an inlet hose (not shown). This inlet hose is connected to the source of adhesive pellets (not shown), such as the fill system 52 schematically shown in these Figures. The cyclonic separator unit 14 includes a generally cylindrical pipe 72 including a top end 74 and a bottom end 76 communicating with the receiving space 16. A sidewall opening 78 located in the pipe 72 proximate to the top end 74 is connected to a tangential inlet pipe 80, which is configured to be coupled to the free end of the inlet hose. The top end 74 includes a top opening 82 connected to an exhaust pipe 84 that extends partially into the space within the generally cylindrical pipe 72 adjacent the top end 74. An air filter 86 may be located within the exhaust pipe 84 and above the top end 74 to filter air flow that is exhausted from the cyclonic separator unit 14. Consequently, the cyclonic separator unit 14 receives adhesive pellets driven by a rapidly moving air stream through the tangential inlet pipe 80 and then decelerates the flow of air and pellets as these rotate downwardly in a spiral manner along the wall of the generally cylindrical pipe 72. The pellets and air are deposited within the receiving space 16 and the air returns through the center of the generally cylindrical pipe 72 to be exhausted through the exhaust pipe 84 and the air filter 86. An exemplary embodiment of the specific components and operation of the cyclonic separator unit 14 is described in further detail in co-pending U.S. patent application Ser. No. 13/799,788 to Chau et al., entitled "Adhesive Dispensing Device Having Optimized Cyclonic Separator Unit", the disclosure of which is hereby incorporated by reference herein in its entirety. It will be understood that the cyclonic separator unit 14 may be omitted from the melt subassembly 12 in some embodiments of the adhesive dispensing device 10.

The receiving space 16 defines a generally rectangular box-shaped enclosure or hopper 16 with an open bottom 90 communicating with the heater unit 20 and a closed top wall 92 having an inlet aperture 94 configured to receive the bottom end 76 of the generally cylindrical pipe 72 of the cyclonic separator unit 14. The receiving space 16 also includes the level sensor 18, which is a capacitive level sensor in the form of a plate element 96 mounted along one of the peripheral sidewalls 98 of the receiving space 16. The plate element 96 includes one driven electrode 100, and a portion of the sidewall 98 or another sidewall 98 of the receiving space 16 acts as a second (ground) electrode of the level sensor 18. For example, the plate element 96 may also include a ground electrode in some embodiments. The level sensor 18 determines the amount or level of adhesive material in the receiving space 16 by detecting with the plate element 96 where the dielectric capacitance level changes between the driven electrode 100 and ground (e.g., open space or air in the receiving space 16 provides a different dielectric capacitance than the adhesive material in the receiving space 16). Although the term "hopper" is used in places during the description of embodiments of the adhesive dispensing device 10, it will be understood that alternative structures/receiving spaces may be provided for feeding the solid adhesive from the fill system 52 into the heater unit 20.

The plate element 96 may be mounted along substantially an entire sidewall 98 at least partially defining the receiving space 16 in order to provide more rapid heat conduction to the plate element 96 for melting off build up of pellets or adhesive material, when necessary. For example, the plate element 96 may be mounted along a sidewall at least partially defining the receiving space 16 such that the level sensor 18 defines a ratio of the surface area of the driven electrode 100 to the surface area of the sidewall defining the receiving space 16 of about 0.7 to 1. In this regard, the surface area of the driven electrode 100 is about 70% of the surface area of the sidewall 98 defining the receiving space 16. Moreover, the large surface area sensed by the plate element 96 provides more accurate and dependable level sensing, which enables more accurate and timely delivery of adhesive material to the melt subassembly 12 when needed. To this end, the broader sensing window provided by the large size of the driven electrode 100 relative to the size of the receiving space 16 also enables more precise control by sensing various states of fill within the receiving space 16, which causes different control actions to be taken depending on the current state of fill within the receiving space 16. The broader sensing window is also more responsive to changes in fill level, which can rapidly change during periods of high output from the adhesive dispensing device 10. Therefore, one or more desired amounts of adhesive material in the receiving space 16 (for example, 30% to 60% filled) may be maintained during operation of the adhesive dispensing device 10. Thus, it is advantageous to make a broader sensing window by maximizing the surface area of the driven electrode 100 relative to the surface area of the sidewall 98 defining the receiving space 16. The specific components and operation of the level sensor 18 and the receiving space 16 are described in further detail with reference to FIGS. 6 through 8 below.

The heater unit 20 is positioned adjacent to and below the receiving space 16 such that the heater unit 20 receives adhesive material flowing downwardly through the open bottom 90 of the receiving space 16. The heater unit 20 includes a peripheral wall 108 and a plurality of partitions 110 extending across the space defined by the peripheral wall 108 between the receiving space 16 and the reservoir 22. As most clearly illustrated in FIGS. 3, 5, and 6, each of the partitions 110 defines a generally triangular cross-section that narrows towards an upstream end 112 facing the open bottom 90 of the receiving space 16 and broadens towards a downstream end 114 facing the reservoir 22. The partitions 110 divide the space between the receiving space 16 and the reservoir 22 into a plurality of openings 116 configured to enable flow of the adhesive material to the reservoir 22. The openings 116 are small enough adjacent the downstream ends 114 of the partitions 110 to force most of the adhesive material into contact with one of the partitions 110. The partitions 110 are cast with the peripheral wall 108 from aluminum in the exemplary embodiment, although it will be appreciated that different heat conductive materials and different manufacturing or machining methods may be used to form the heater unit 20 in other embodiments.

In this regard, the heater unit 20 of the exemplary embodiment is in the form of a heater grid. It will be understood that the plurality of openings 116 may be defined by different structure than grid-like partitions in other embodiments of the heater unit 20, including, but not limited to, fin-like structures extending from the peripheral wall 108, without departing from the scope of the invention. In this regard, the "heater unit" 20 may even include a non grid-like structure for heating the adhesive in other embodiments of the invention, as the only necessary requirement is that the heater unit 20 provide one or more openings 116 for flow of adhesive through the adhesive dispensing device 10. In one alternative, the partitions 110 could be replaced by fins extending inwardly from the peripheral wall 108, as is typically the case in larger sized heater grids used in larger melting devices. It will be understood that the heater unit 20 may be separately formed and coupled to the receiving space 16 or may be integrally formed as a single component with the receiving space 16 in embodiments consistent with the invention.

Figure 5:
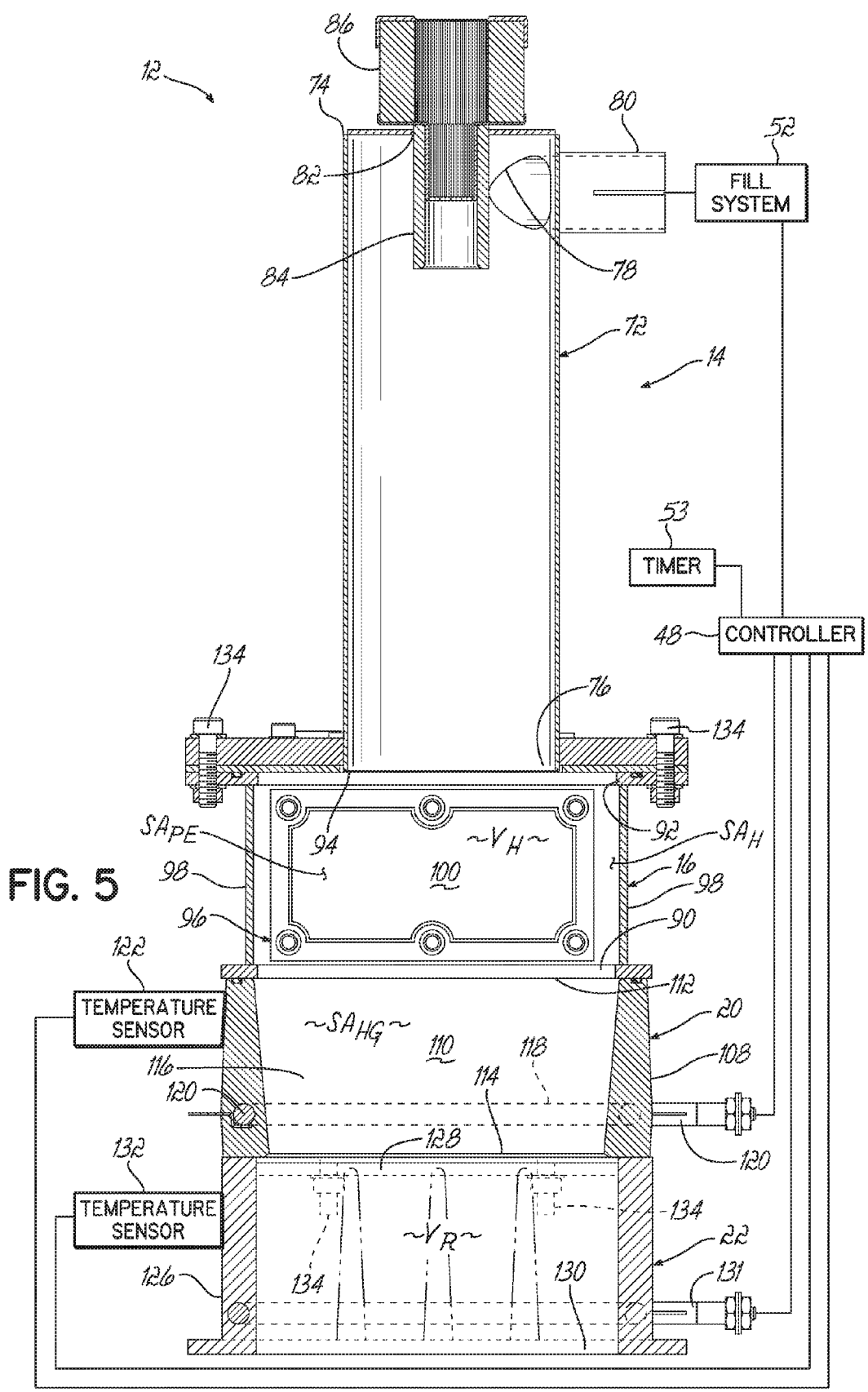
FIG. 5 is a cross-sectional front view of the melt subassembly of FIG. 4.
Figure 6:
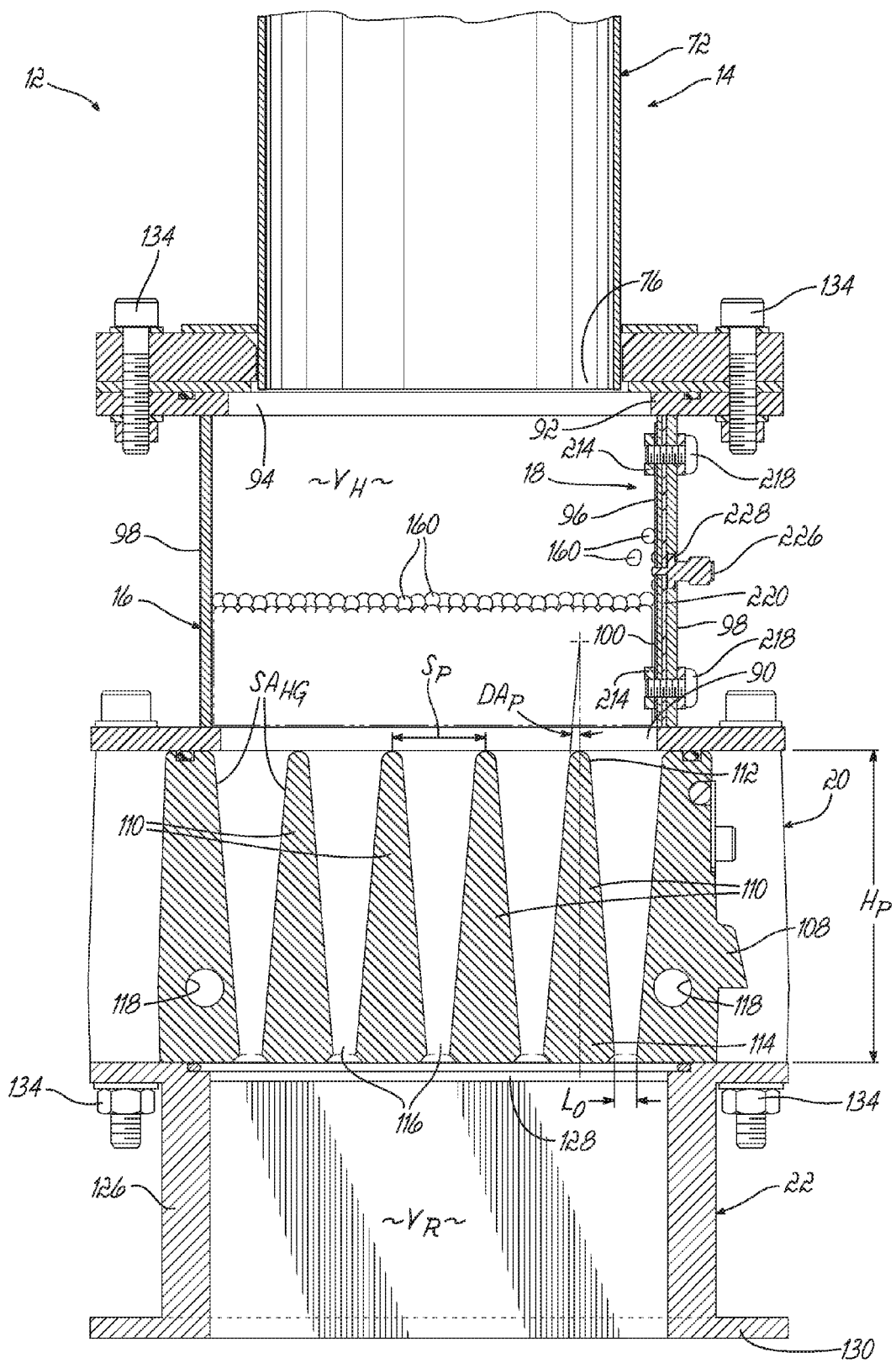
FIG. 6 is a cross-sectional side view of the melt subassembly of FIG. 4.

The heater unit 20 is designed to optimize the heating and melting of adhesive material flowing through the adhesive dispensing device 10. To this end, the peripheral wall 108 includes a hollow passage 118 as shown in FIGS. 5 and 6 and configured to receive a heating element 120 such as a resistance heater, a tubular heater, a heating cartridge, or another equivalent heating element, which may be inserted or cast into the heater unit 20. The heating element 120 receives signals from the controller 48 and applies heat energy to the heater unit 20, which is conducted through the peripheral wall 108 and the partitions 110 to transfer heat energy to the adhesive material along the entire surface area defined by the heater unit 20. For example, the exemplary embodiment of the heater unit 20 includes a temperature sensor 122 to detect the temperature of the heater unit 20. The temperature sensor 122 is positioned to sense the temperature at the peripheral wall 108 and may indirectly sense the adhesive temperature as well, although it will be understood that the adhesive temperature tends to lag behind the temperature changes of the heater unit 20 by a small margin. In other non-illustrated embodiments, the temperature sensor 122 may include different types of sensors, such as a probe extending into the adhesive. To this end, the temperature sensor 122 provides regular feedback on a unit temperature for use in controlling the heating element 120. The heat energy is also conducted through the reservoir 22 and the receiving space 16, which helps maintain the temperature of the molten adhesive in the reservoir 22 and helps melt off any adhesive material inadvertently stuck in the receiving space 16 (such as on the plate element 96 of the level sensor 18). The design of the heater unit 20 and the partitions 110 also improves the start up process following a shut down or standby of the adhesive dispensing device 10 by more rapidly providing heat energy to the adhesive material in the receiving space 16 and in the reservoir 22 (which may be solidified during shut down) as well as the adhesive material in the heater unit 20. In the exemplary embodiment, the heater unit 20 is operable to bring the entire melt subassembly 12 up to operating temperature from a standby state with a warm up time of about 7 minutes, thereby substantially reducing delays caused by lengthy warm up cycles.

In the exemplary embodiment of the heater unit 20 shown in FIGS. 5 and 6, the partitions 110 and openings 116 define several dimensions based upon the method of forming the heater unit 20 and the adhesive material chosen for dispensing. In this regard, the heating element 120 used with the exemplary embodiment defines a minimum bend radius of 0.375 inches, so the spacing $S_P$ between the centers of adjacent partitions 110 is chosen to be 0.75 inches to enable the heating element 120 to bend between each adjacent partition 110. The casting process defines a minimum draft angle for the angling of the partitions 110, and a draft angle close to this minimum draft angle is chosen for the partitions 110 in the heater unit 20. To this end, the draft angle $DA_P$ of the partitions 110 is about 5 degrees in the exemplary embodiment. The openings 116 between the partitions 110 define an opening length $L_O$ of about 0.156 inches, and this opening length $L_O$ was chosen to collectively provide a total opening for flow in the heater unit 20 that is configured to provide an acceptable pressure drop and a sufficient volume flow of the adhesive when operating at a high throughput. The draft angle $DA_P$ and opening length $L_O$ determine how tall each of the partitions 110 will be. For example, the partitions 110 of the exemplary embodiment define a height $H_P$ of about 2.5 inches. It will be understood that the opening length $L_O$ and the other dimensions may be modified in other embodiments consistent with the invention, such as when the viscosity of the adhesive being used is modified and therefore requires a larger overall through-opening in the heater unit 20. The dimensions of the elements of the heater unit 20 may also be further modified from this exemplary embodiment to adjust the effective surface area $SA_{HG}$ of the heater unit 20 and thereby modify the melt rate for the adhesive, regardless of the size and shape of adhesive pellets used.

The reservoir 22 is positioned adjacent to and below the heater unit 20 such that the reservoir 22 receives adhesive material flowing downwardly through the openings 116 defined in the heater unit 20. The reservoir 22 includes a peripheral wall 126 extending between an open top end 128 and an open bottom end 130. The reservoir 22 may optionally include partitions or fins projecting inwardly from the peripheral wall 126 in some embodiments (shown in phantom in the Figures). The open top end 128 communicates with the heater unit 20 adjacent to the downstream ends 114 of the partitions 110. The open bottom end 130 is bounded by the manifold 54 and thereby provides communication of molten adhesive material into the conduits 58 of the manifold 54. Similar to the heater unit 20, the reservoir 22 may also be manufactured from aluminum such that heat from the heater unit 20 is conducted along the peripheral wall 126 for maintaining the temperature of the molten adhesive in the reservoir 22. In addition, a reservoir heating device in the form of a heating element 131 may be provided in the peripheral wall 126 to further heat or maintain the melted adhesive in the reservoir 22 at the elevated application temperature. To this end, the heating element 131 may include a resistance heater, a tubular heater, a heating cartridge, or another equivalent heating element, which may be inserted or cast into the reservoir 22. However, other heat conductive materials and other manufacturing methods may be used in other embodiments consistent with the scope of the invention. It will be understood that the heater unit 20 may be separately formed and coupled to the reservoir 22 or may be integrally formed as a single component with the reservoir 22 in embodiments consistent with the invention.

Figure 4:
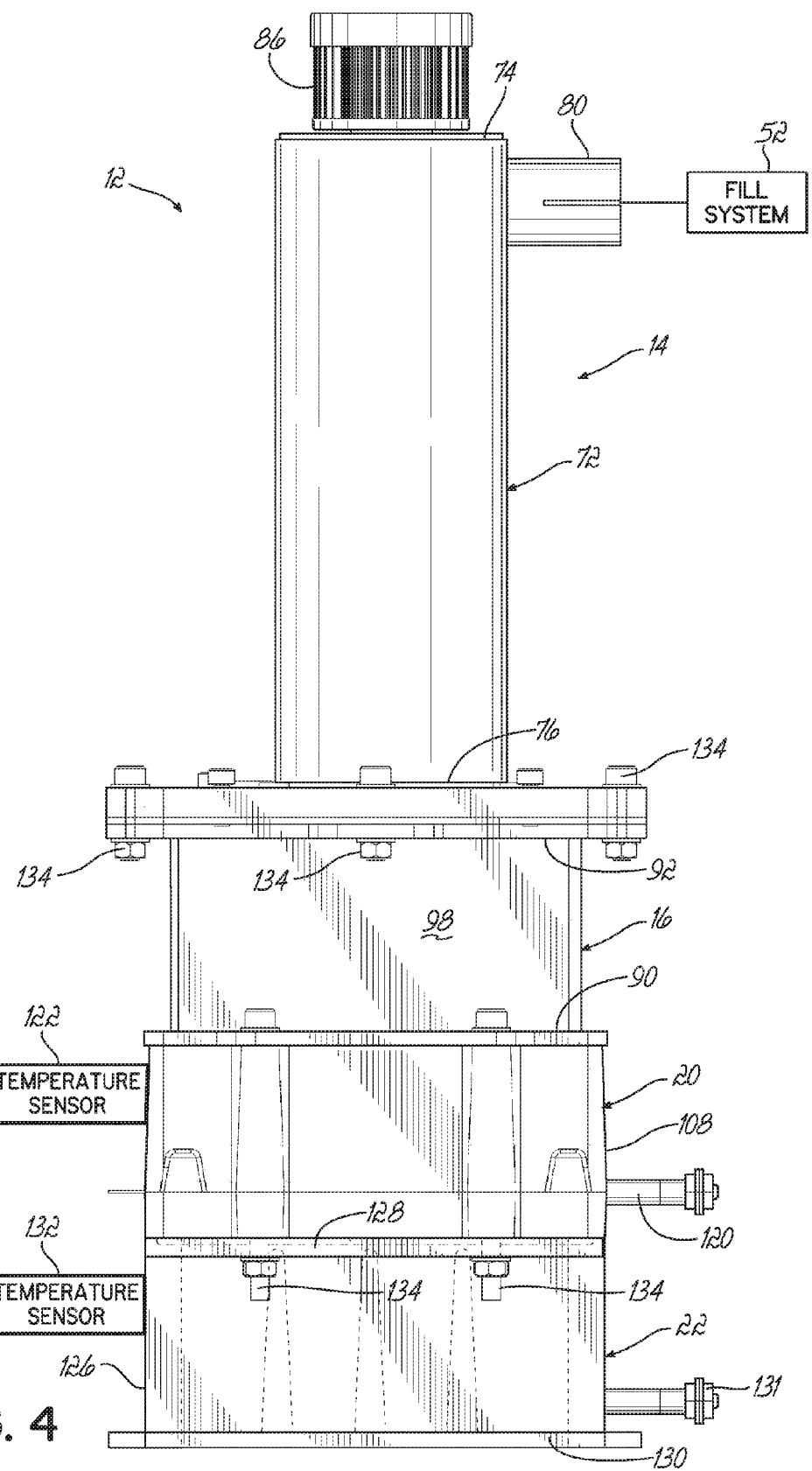
FIG. 4 is a front view of the melt subassembly of FIG. 3.

The reservoir 22 may include one or more sensors configured to provide operational data to the controller 48 such as the temperature of the adhesive material in the reservoir 22. For example, the exemplary embodiment of the reservoir 22 includes a temperature sensor 132 to detect the temperature of the reservoir 22. The temperature sensor 132 is positioned to sense the temperature at the peripheral wall 126 and may indirectly sense the adhesive temperature as well, although it will be understood that the adhesive temperature tends to lag behind the temperature changes of the reservoir 22 by a small margin. In other non-illustrated embodiments, the temperature sensor 132 may include different types of sensors, such as a probe extending into the adhesive. This detected temperature may be communicated to the controller 48 and used to control the heat energy output by the heating element 131 in the reservoir, or also the heat energy output by the heating element 120 of the heater unit 20. It will be understood that a plurality of additional sensors may be located within the various elements of the melt subassembly 12 for communication with the controller 48 to monitor the accurate operation of the adhesive dispensing device 10. However, a generally expensive level sensor for use below the heater unit 20 is not necessary in the exemplary embodiment in view of the highly accurate measurements of adhesive level in the receiving space 16 that are enabled by the capacitive level sensor 18. As shown in FIG. 4, the reservoir 22, heater unit 20, receiving space 16, and cyclonic separator unit 14 are coupled together with a plurality of threaded fasteners 134 connecting the peripheries of these elements. However, it will be understood that alternative fasteners or methods of coupling (or integral forming of) these elements together may be used in other embodiments.

As briefly described above, the manifold 54 is located adjacent to and below the open bottom end 130 of the reservoir 22 so as to provide fluid communication from the reservoir 22 to the pump 56 and then to the outlets 60. To this end, the manifold 54 is machined from an aluminum block to include a plurality of conduits 58 (one of which is shown in FIG. 3) extending between these various elements of the melt subassembly 12. It will be understood that the manifold 54 may further include additional elements (not shown) in some embodiments, such as valves for controlling the flow of adhesive material to and from the pump 56 and supplemental heating elements for maintaining the temperature of the molten adhesive in the conduits 58. It will be understood that all or a portion of the manifold 54 may be separately formed and coupled to the reservoir 22 or may be integrally formed as a single component with the reservoir 22 in embodiments consistent with the invention.

The pump 56 is a known double-acting pneumatic piston pump that is positioned adjacent to and alongside the previously described elements of the melt subassembly 12. More specifically, the pump 56 includes a pneumatic chamber 140, a fluid chamber 142, and one or more seals 144 of seal cartridges disposed between the pneumatic chamber 140 and the fluid chamber 142. A pump rod 146 extends from the fluid chamber 142 to a piston 148 located within the pneumatic chamber 140. Pressurized air is delivered in alternating fashion to the upper and lower sides of the piston 148 to thereby move the pump rod 146 within the fluid chamber 142, causing drawing of molten adhesive into the fluid chamber 142 from the reservoir 22 and expelling of the molten adhesive in the fluid chamber 142 to the outlets 60. The pressurized air may be delivered through an inlet hose 150 and controlled by a spool valve 151 (only the outer housing of which is shown) shown most clearly in FIG. 2. The fluid chamber 142 may also include a check valve leading back to the reservoir 22 to deliver any adhesive that would otherwise leak from the fluid chamber 142 back into the reservoir 22. The pump 56 may be controlled by the controller 48 to deliver the desired flow rate of adhesive material through the outlets 60 as well understood in the dispenser field. More particularly, the pump 56 may include a control section 152 containing a shifter 153 (partially shown in FIG. 3) used to mechanically actuate changes in directional movement for the piston 148 and the pump rod 146 near the end limit positions of these elements. One exemplary embodiment of the specific components and operation of the pump 56 and the control section 152 is described in further detail in co-pending U.S. patent application Ser. No. 13/799,656 to Estelle, entitled "Adhesive Dispensing System and Method Including A Pump With Integrated Diagnostics", the disclosure of which is hereby incorporated by reference herein in its entirety. Additional diagnostics for the adhesive dispensing device 10 may be enabled by monitoring actuation signals for the downstream guns or modules with the controller 48, and an exemplary process for this is described in further detail in co-pending U.S. patent application Ser. No. 13/799,694 to Beal et al., entitled "Dispensing Systems and Methods for Monitoring Actuation Signals for Diagnostics", the disclosure of which is hereby incorporated by reference herein in its entirety.

In operation, the heater unit 20 is brought up to temperature by the heating element 120 and heat energy is conducted into the receiving space 16 and the reservoir 22 to bring those elements and the adhesive material contained within up to the desired elevated application temperature. The reservoir 22 may also be brought up to temperature by the heating element 131 located at the reservoir 22, as discussed above. It will be understood that the controller 48 may operate the heating elements 120, 131 to perform a smart melt mode to further enhance the reduction of char and degradation of the adhesive. One exemplary embodiment of the specific components and operation of the controller 48 in such a smart melt mode is described in further detail in co-pending U.S. patent application Ser. No. 13/799,737 to Bondeson et al., entitled "Adhesive Dispensing System and Method Using Smart Melt Heater Control", the disclosure of which is hereby incorporated by reference herein in its entirety. The controller 48 will receive a signal from the temperature sensor 132 when the elevated application temperature has been reached, which indicates that the melt subassembly 12 is ready to deliver molten adhesive. The pump 56 then operates to remove molten adhesive material from the open bottom end 130 of the reservoir 22 as required by the downstream guns or modules (not shown) connected to the outlets 60. As the pump 56 removes adhesive material, gravity causes at least a portion of the remaining adhesive material to move downwardly into the reservoir 22 from the receiving space 16 and the openings 116 in the heater unit 20. The lowering of the level of adhesive pellets 160 (or melted adhesive material) within the receiving space 16 is sensed by the level sensor 18, and a signal is sent to the controller 48 indicating that more adhesive pellets 160 should be delivered to the melt subassembly 12. The controller 48 then sends a signal that actuates delivery of adhesive pellets 160 from the fill system 52 through the cyclonic separator unit 14 and into the receiving space 16 to refill the adhesive dispensing device 10. This process continues as long as the adhesive dispensing device 10 is in active operation.

Advantageously, the melt subassembly 12 of the adhesive dispensing device 10 has been optimized to hold a reduced amount of adhesive material at the elevated application temperature compared to conventional dispensing devices. To this end, a combination of optimized features in the melt subassembly 12 enables the same maximum adhesive throughput as conventional designs with up to 80% less adhesive material being retained within the melt subassembly 12. This combination of features includes the improved reliability of the adhesive filling system (e.g., the cyclonic separator unit 14 and the receiving space 16) enabled by the capacitive level sensor 18 and the smaller sized receiving space 16; the design of the heater unit 20 including the partitions 110; the design of the smaller sized reservoir 22; and smart melt technology run by the controller 48 to refill the melt subassembly 12 with adhesive material as rapidly as needed. With these features in combination, the total retained volume of adhesive material (both molten adhesive and adhesive pellets 160) held within the melt subassembly 12 is approximately 2 liters, which is significantly less than conventional dispensing devices and melting devices which require about 10 liters of adhesive material to be held at the elevated application temperature. Consequently, significantly less adhesive material is held at the elevated application temperature, thereby reducing the likelihood that adhesive material will remain in the melt subassembly 12 long enough to become degraded or charred by staying at the high temperature over a long period of time. In addition, the smaller volume of retained adhesive material enables the melt subassembly 12 to be brought to the elevated application temperature during a warm-up cycle much quicker than conventional designs which need to heat significantly more adhesive material during warm up.

In the exemplary embodiment as shown in FIG. 5, the receiving space 16 may define a hopper volume $V_H$ and the reservoir 22 may define a reservoir volume $V_R$. The heater unit 20 defines a total heater grid surface area $SA_{HG}$ at the partitions 110 and at the peripheral wall 108 that actively applies heat energy by contacting the adhesive material within the heater unit 20. In the adhesive dispensing device 10 of the current invention, the relation of the combined volumes of the receiving space 16 and of the reservoir 22 ($V_H+V_R$) to the total heater grid surface area $SA_{HG}$ is minimized as much as possible while still enabling the maximum adhesive flow necessary during periods of high adhesive need. For example, the hopper volume $V_H$ in the exemplary embodiment is about 54 cubic inches, the reservoir volume $V_R$ in the exemplary embodiment is about 35 cubic inches, and the heater grid surface area $SA_{HG}$ in the exemplary embodiment is about 130 square inches. Thus, the relation of combined volumes to total heater grid surface area in the exemplary embodiment is (54+35)/130=approximately 0.685 cubic inches of volume to 1 square inch of surface area. By comparison, this relation of combined volumes to total heater grid surface area in conventional adhesive dispensing devices typically ranges from about 3 cubic inches of volume to 1 square inch of surface area, to about 3.5 cubic inches of volume to 1 square inch of surface area as a result of the larger retained volume within the melt subassemblies of those conventional designs (and likely also less surface area on conventional heater units). By optimizing or minimizing this relation, the total amount of adhesive material held at elevated application temperatures within the melt subassembly 12 is also minimized, leading to the benefits described above. Moreover, the melt rate of solid adhesive material within the receiving space 16 is increased such that a maximum flow rate of adhesive can still be achieved despite the lower retained volume of molten adhesive material.

The melt subassembly 12 of the exemplary embodiment is also optimized for the particular size and shape of adhesive pellets 160 used in the adhesive dispensing device 10. In this regard, 3 to 5 millimeter diameter round-shaped adhesive pellets 160 are used with the melt subassembly 12 of the exemplary embodiment. However, it will be understood that other shapes and sizes of adhesive pellets 160 may be used in other embodiments, including, but not limited to, pillow-shaped, slat-shaped, chicklet-shaped, and other shapes pellets up to a size of 12 millimeters in cross-sectional dimension. In the exemplary embodiment, the small diameter size of the adhesive pellets 160 enables a reduction in the pipe size (e.g., inlet hose) and air flow velocity required to lift and move the adhesive pellets 160 from the source into the melt subassembly 12. This smaller velocity air is easier to slow down in the cyclonic separator unit 14 to remove the adhesive pellets 160 from the air flow for use in the receiving space 16. The round shape of the adhesive pellets 160 is preferred over other shapes such as pillow-shaped because the round shape avoids geometry-based interlocking or bridging together of the adhesive pellets 160. Moreover, the pile of round adhesive pellets 160 within the receiving space 16 tends to entrap less air than other shapes of pellets, which renders the level sensor 18 more likely to accurately sense the difference in dielectric capacitance between the portion of the receiving space 16 with adhesive pellets 160 and the portion of the receiving space 16 without adhesive pellets 160. Thus, the optimization of the features of the melt subassembly 12 is further benefitted by the selection of the optimized adhesive pellet 160 to use with the adhesive dispensing device 10.

Accordingly, the melt subassembly 12 as a whole has been optimized compared to conventional adhesive dispensing devices. More particularly, the melt subassembly 12 minimizes the amount of adhesive material that needs to be retained and held at the elevated application temperature within the adhesive dispensing device 10 while still enabling a maximum adhesive flow to be achieved during periods of high adhesive need. The smaller volumes of the receiving space 16 and the reservoir 22 enable quicker warm up from a cold start and reduce the likelihood that any of the adhesive material will be degraded or charred by being held at the elevated application temperature for too long a period of time. Despite the lower volume of adhesive material on hand within the melt subassembly 12, the accurate monitoring of adhesive level within the receiving space 16 enables the controller 48 to request more adhesive material quickly so that the receiving space 16 and the reservoir 22 never run out of molten adhesive material to deliver to the pump 56 and the outlets 60.

Figure 7:
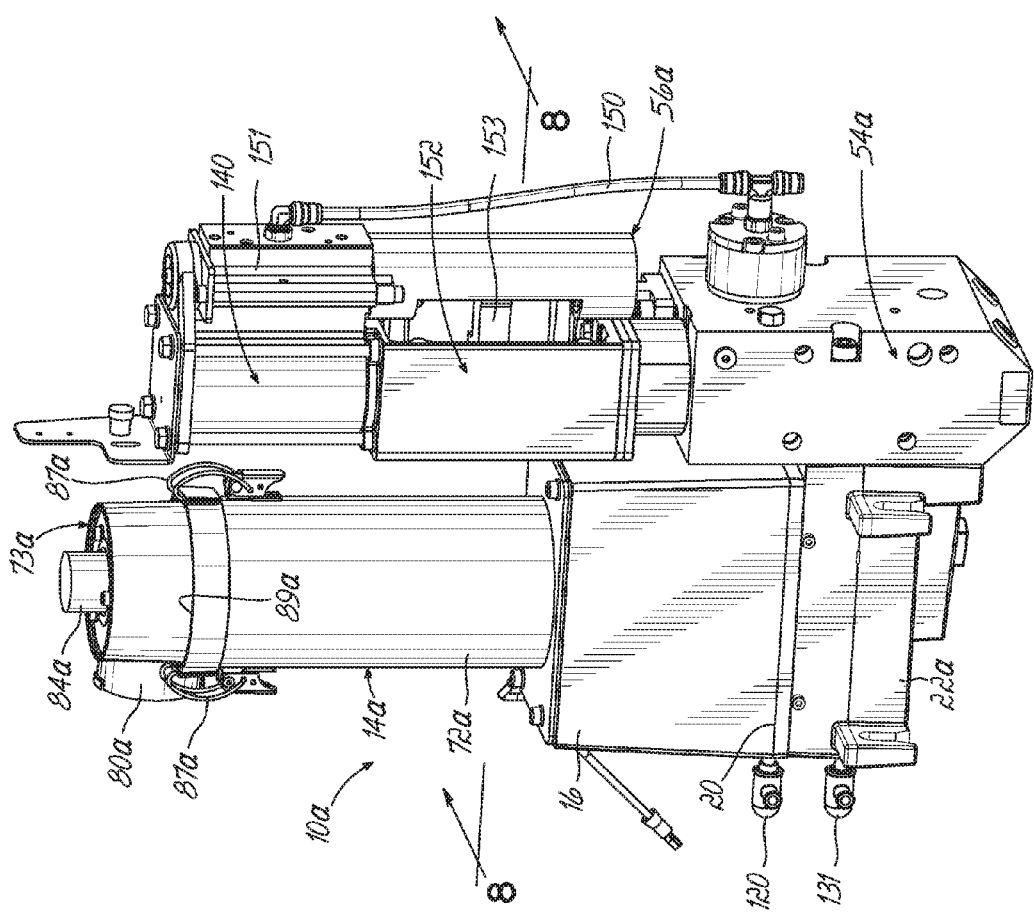
FIG. 7 is a perspective view of an alternative embodiment of the adhesive dispensing device, including a similar melt subassembly as the embodiment of FIGS. 1 through 6.
Figure 8:
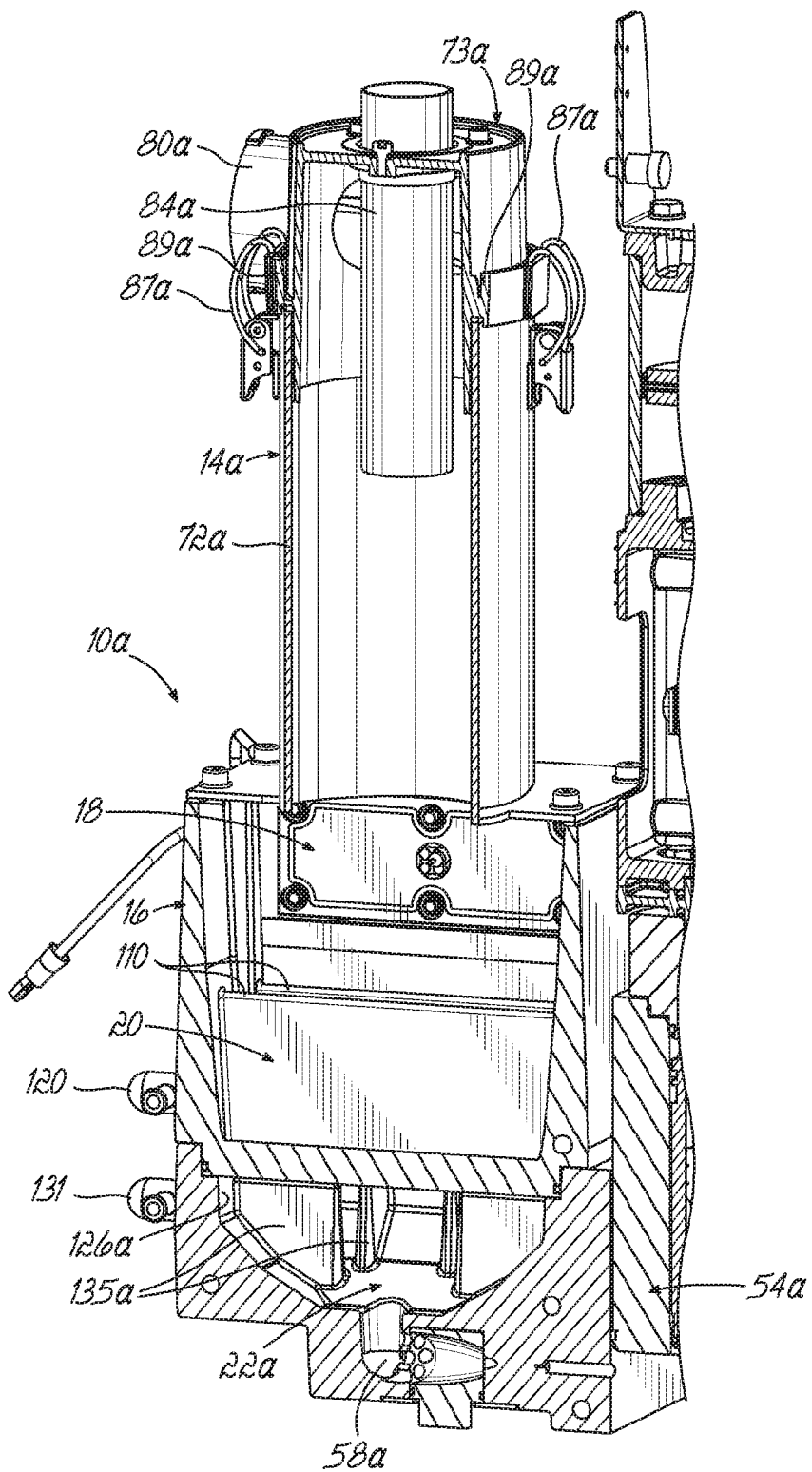
FIG. 8 is a cross-sectional perspective view of a portion of the adhesive dispensing device of FIG. 7 taken along line 8-8.

With reference to FIGS. 7 and 8, another exemplary embodiment of the adhesive dispensing device 10a is shown in detail. This embodiment of the adhesive dispensing device 10a includes many of the same elements as the previously-described embodiment of FIGS. 1 through 6, and these elements are shown with identical reference numbers without further description below when the elements are unchanged from the previous embodiment. Modified elements including the adhesive dispensing device 10a itself are provided with similar reference numbers followed by an "a" to highlight the modified components. These modified and additional components are described in detail below.

Beginning with reference to the right-hand side of FIG. 7, the pump 56a is slightly modified from what was shown in the wall-mounted context of the embodiment of FIG. 1. To this end, the pump 56a includes a combined fluid chamber and manifold 54a in addition to the pneumatic chamber 140 and the control section 152. To this end, the combined fluid chamber and manifold 54a replace the separate fluid chamber 124 and manifold 54 of the previous embodiment, thereby simplifying the total amount of structure that must be provided in the adhesive dispensing device 10a. As noted above, the shifter 153 may be a mechanical shifter that changes air flow direction at the piston 148 by actuating the spool valve 151 to switch positions when limit switches are engaged, but it will also be understood that the shifter 153a may be modified in other embodiments, such as to include electronic shifters controlled by various types of sensors. Regardless of the particular structure used with the shifter 153a, the pump 56a operates in the same manner as described above to remove melted adhesive from the reservoir 22a via the flow passage 58a and through the combined fluid chamber and manifold 54a.

In the dispensing device 10a shown in FIGS. 7 and 8, the cyclonic separator unit 14a has also been modified. In this regard, the various structures that were welded into position on the generally cylindrical pipe 72a have been removed from the generally cylindrical pipe 72a and formed into a removable cyclone cap 73a. More particularly, the exhaust pipe 84a and the tangential inlet pipe 80a have been integrally formed or connected to the removable cyclone cap 73a. The cyclone cap 73a defines an inner diameter slightly smaller than the diameter of the generally cylindrical pipe 72a so that the cyclone cap 73a can be at least partially inserted into the generally cylindrical pipe 72a. The generally cylindrical pipe 72a includes one or more retention clips 87a configured to engage with a corresponding retention lip 89a formed in the outer periphery of the cyclone cap 73a when the cyclone cap 73a is inserted into the generally cylindrical pipe 72a. As a result, the cyclone cap 73a may be selectively removed so that the generally cylindrical pipe 72a and the receiving space 16 may be easily inspected when necessary. The provision of the cyclone cap 73a also simplifies manufacturing of the cyclonic separator unit 14a because welding the elements into position on the generally cylindrical pipe 72a is no longer necessary. In all other respects, the cyclonic separator unit 14a operates similarly to the previous embodiment described above.

Although the receiving space 16 and the heater unit 20 are identical to those previously described, the reservoir 22a has also been slightly modified in this embodiment of the dispensing device 10a. Instead of a completely open box-like flow path being formed between the heater unit 20 and the manifold 54a, the reservoir 22a of this embodiment includes a plurality of fins 135a projecting inwardly from the peripheral wall 126a to increase the surface area that may be heated by the heating element 131 in the manifold 22a. The peripheral wall 126a tapers inwardly to form a bowl-shape flow path leading from the bottom of the heater unit 20 to the manifold 54a. Thus, the reservoir 22a also further minimizes the volume of adhesive held in the dispensing device 10a, which is advantageous for the reasons set forth above. For at least these reasons, the dispensing device 10a of this alternative embodiment shown in FIGS. 7 and 8 continues to achieve the advantages of the previously described embodiment.

Figure 9:
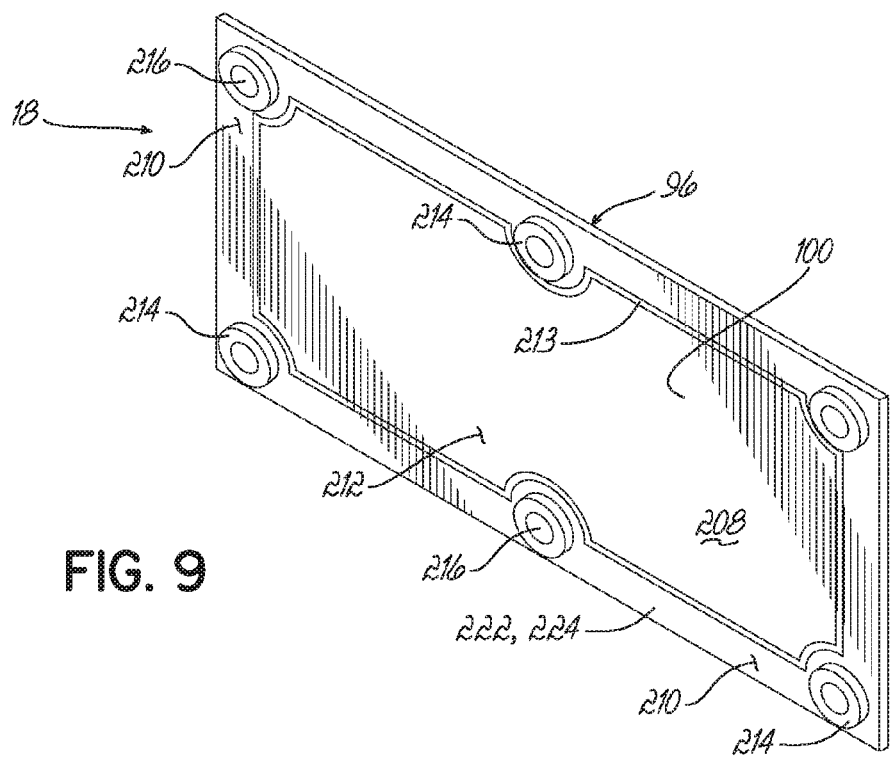
FIG. 9 is a front perspective view of the level sensor installed within the melt subassembly of FIGS. 3 and 8.
Figure 10:
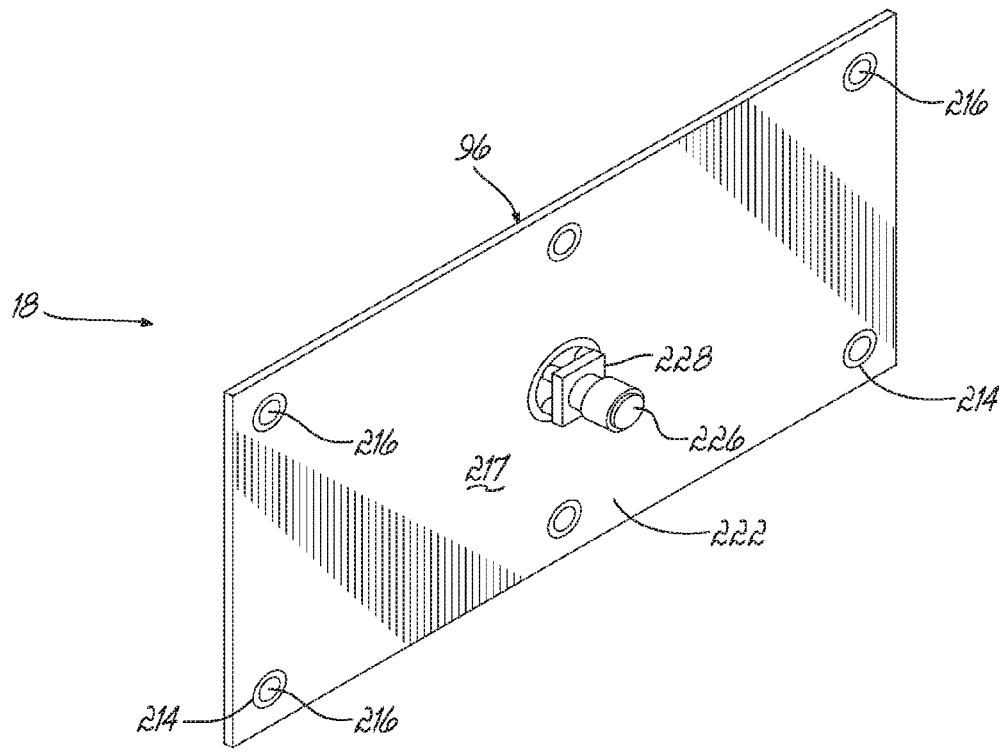
FIG. 10 is a rear perspective view of the level sensor of FIG. 9.

FIGS. 6, 9, and 10 show additional features of the capacitive level sensor 18. The level sensor 18 includes the plate element 96, which has a front face 208 including an outer portion 210 electrically separated from an inner portion 212 by an electric barrier 213. According to the exemplary embodiment of the invention, the level sensor 18 is a printed circuit board manufactured from materials capable of withstanding the high temperatures within the receiving space 16. One example of such a material is copper, although other materials could be used in other embodiments consistent with the scope of the invention. Furthermore, the exemplary embodiment of the level sensor 18 measures a fill level within the receiving space 16 having the plurality of sidewalls 98. However, it will be appreciated that the level sensor 18 may be used with any tank having at least one tank wall, such as a rectangular tank or a cylindrical tank.

In order to mount the level sensor 18 within the receiving space 16, the outer portion 210 includes a plurality of fastener mounts 214 pressed into the plate element 96. The plurality of fastener mounts 214 is symmetrically affixed about the outer portion 210 of the level sensor 18. Each of the fastener mounts 214 further includes a mount aperture 216 extending through the plate element 96 from the front face 208 to a rear face 217. A plurality of sensor fasteners 218 are fastened within the mount apertures 216 in order to mount the level sensor 18 within the receiving space 16 and located adjacent one of the peripheral sidewalls 98 of the receiving space 16. For example, the mount apertures 216 and the sensor fasteners 218 may be threaded such that the sensor fasteners 218 are screwed into position in the mount apertures 216.

Furthermore, a gasket 220, such as a gasket made of synthetic rubber and fluoropolymer elastomer (e.g., Viton®), is sandwiched between the rear face 217 of level sensor 18 and the sidewall 98 to seal the level sensor 18 against the sidewall 98. Accordingly, the plate element 96 is sized for being positioned substantially flush against the sidewall 98 and sealed against the sidewall 98 using the gasket 220. The gasket 220 prevents any adhesive material from pooling along the rear face 217. As previously described herein and as shown in FIG. 6, the positioning and size of the circuit board plate element 96 enables the plate element 96 to be efficiently heated within the receiving space 16 in order to minimize the build-up of the adhesive pellets 160 on the level sensor 18 by melting the adhesive pellets 160 off of the front face 208. More specifically, the heat conducted from the heater unit 20 through the peripheral sidewalls 98 of the receiving space 16 is readily conducted into the large level sensor 18 to quickly melt off any adhesive pellets 160 or material stuck on the plate element 96 above the level of adhesive in the receiving space 16 (which would otherwise affect the dielectric capacitance sensed at those locations). As a result, any collection of adhesive pellets 160 or adhesive material above the actual fill level within the receiving space 16 will rapidly melt off to avoid affecting the readings of the actual fill level within the receiving space 16.

The large level sensor 18 is sized such that the level sensor 18 engages a majority, or more than 40%, of the surface area of the sidewall 98 onto which the level sensor 18 is mounted. More particularly, the large level sensor 18 engages more than 70% or almost the entire surface area of the sidewall 98 onto which the level sensor is mounted. In the exemplary embodiment, for example, the driven electrode 100 of the plate element 96 may define a surface area $SA_{PE}$ of about 7.5 square inches and the sidewall 98 of the receiving space 16 may define a sidewall surface area $SA_H$ of about 10.7 square inches, such that the level sensor 18 defines a ratio of the surface areas of about 0.7 to 1. This ratio of surface areas provides a broader sensing window for the level sensor 18 located within the receiving space 16. In other words, the level sensor 18 is capable of detecting a change in dielectric capacitance indicating a change in fill level of adhesive over a large percentage of the surface area of the sidewall of the receiving space 16. This broader sensing window is more reliably responsive to fill level changes as localized adhesive buildup and other localized effects do not substantively affect the overall sensor output. Furthermore, the sensitivity of the readings of the level sensor 18 is increased such that a better signal-to-noise ratio is achieved when reading the dielectric capacitance within the receiving space 16 and producing an analog signal. Consequently, it is advantageous to make a broader sensing window by maximizing the surface area of the driven electrode 100 relative to the surface area of the sidewall 98. Furthermore, the larger sensing window provides better sensing capabilities than the smaller probe-like sensors used in conventional hoppers.

In addition, this broader sensing window enables additional controls to be performed using the level sensor 18. In this regard, the level sensor 18 in the exemplary embodiment may be configured to enable generation of a first control signal when the fill level in the receiving space 16 is low enough to prompt delivery of more adhesive material to the receiving space (for example, at 40%) and to enable generation of a second control signal when the fill level in the receiving space 16 indicates full filling of the receiving space (for example, at 90%). Thus, rather than just sending a set amount of adhesive material to the receiving space 16 each time a threshold fill level is reached, the level sensor 18 can cause the generation of multiple control signals that guarantee full replenishment of the receiving space 16 regardless of the current throughput rate when the refill process is started. Additional signals for various fill levels may be generated in other embodiments consistent with the invention, and these additional signals may be used, for example, to better detect the rate of throughput and thereby proactively supply adhesive material to the receiving space 16 as the adhesive material is needed. The adhesive dispensing device 10 can then more readily supply and melt the appropriate amount of adhesive material nearly on demand or on an as-used basis. These multiple control signals are effectively enabled by the broader sensing window of the level sensor 18.

It will be appreciated that the level sensor 18 described in detail herein may be used with other types of receiving spaces 16 having various sizes and cross-sectional shapes. When the receiving space 16 is increased in size for another adhesive dispensing device, for example, the level sensor 18 may also be upsized to maintain a similar ratio of surface areas (of the driven electrode 100 and the sidewall 98) and a similar broader sensing window. However, the level sensor 18 may also be used without significant resizing, as long as the size of the driven electrode 100 remains at a sufficient level to provide the multiple control signals described in detail above. To this end, the level sensor 18 preferably maintains a ratio of surface areas above 0.4 to 1, regardless of the size of the receiving space 16. Even in embodiments where the driven electrode 100 covers less than 40% of the sidewall 98 of the receiving space 16, the size of the driven electrode 100 (e.g., a height of the driven electrode 100) will still be sufficient to provide multiple control signals at various fill levels in the receiving space 16. In such circumstances, the level sensor 18 will provide the advantages described above, including better responsiveness, more accurate readings, less susceptibility to localized events such as adhesive buildup, and the generation of multiple control signals.

The inner portion 212 of the level sensor 18 operates as the powered or driven electrode 100 and the outer portion 210 and rear face 217 are both electrically coupled as a ground electrode 222. Thus, the driven electrode 100 and the ground electrode 222 are formed on the same plate element 96. In addition, the ground electrode 222 is electrically coupled to the sidewall 98 of the receiving space 16. The driven electrode 100 and the ground electrode 222 define the capacitive terminals of the level sensor 18 with the air and adhesive pellets 160 acting as the dielectric positioned there between. Generally, the dielectric capacitance of the dielectric sensed between the driven and ground electrodes 100, 222 is sensed where the distance between the driven and ground electrodes 100, 222 is at a minimum. This minimum distance could be defined across the electric barrier 213 or could be defined by a space between the driven electrode 100 and the closest sidewall 98 of the receiving space 16 electrically coupled to the ground electrode 222. Thus, the actual distance through the dielectric between the driven and ground electrodes 100, 222 is dependent on the geometry of the receiving space 16.

Rather than the minimum distance between the driven and ground electrodes 100, 222, this distance may be maximized to increase the amount of dielectric between the driven and ground electrodes 100, 222. Increasing the amount of dielectric between capacitive terminals improves the overall accuracy of the level sensor 18. Thus, rather than depend on the geometry of the receiving space 16 to determine this minimum distance, the level sensor 18 may, in another embodiment, include an electrically driven shield 224 adapted to direct the level sensor 18 to measure the dielectric capacitance between the driven electrode 100 and a predetermined location on the receiving space 16. In this alternative embodiment, the outer portion 210 is operatively powered to act as the driven shield 224. Accordingly, the driven shield 224 produces an electric field circumferentially surrounding the driven electrode 100 such that the driven electrode 100 is forced to sense the dielectric capacitance located between the driven electrode 100 and the sidewall 98 of the receiving space 16 located directly opposite of the driven electrode 100 (or a portion of the receiving space 16 directly opposite the driven electrode 100). Thereby, the distance between the driven and ground electrodes 100, 222 may be increased to improve the accuracy of the level sensor 18. In the exemplary embodiment of the level sensor 18, the driven shield 224 is provided to improve the accuracy and responsiveness of the readings indicating the level of adhesive material within the receiving space 16.

The level sensor 18 also includes an SMA connector 226 to which the driven electrode 100 and the ground electrode 222 are each electrically coupled. In the alternative embodiment, the driven shield 224 is also electrically coupled to the SMA connector 226. The SMA connector 226 is affixed to the plate element 96 and extends from the rear face 217 through the gasket 220 to a connector hole 228 in the sidewall 98. As shown in FIG. 8, the SMA connector 226 extends through the sidewall 98 to provide external access to the SMA connector 226 for operatively connecting the SMA connector 226 to the controller 48 for sensing the changing dielectric capacitance as the level of adhesive pellets 160 changes within the receiving space 16. As described above, the control signal generated by this sensed change in fill level is then used to actuate the delivery of more adhesive material through the cyclonic separator unit 14 (or by other methods as described above), to thereby maintain a desired level of adhesive material in the receiving space 16.

Figure 11:
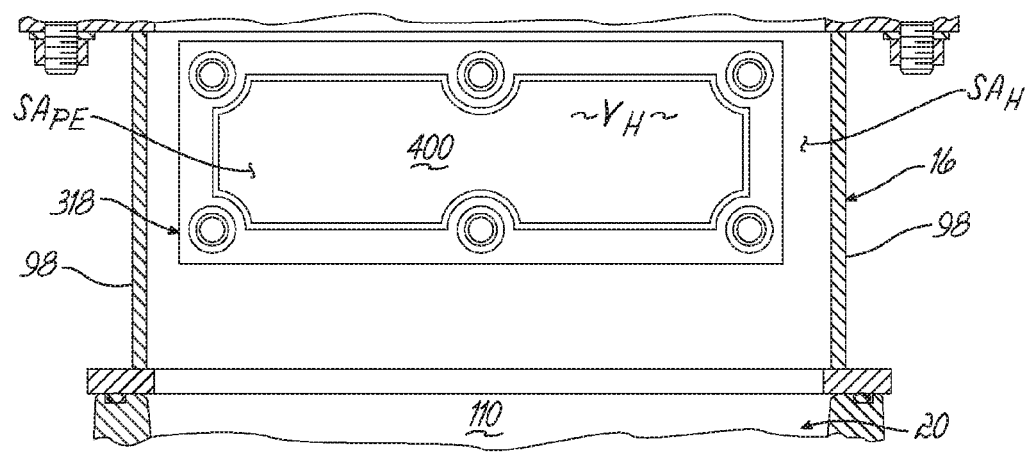
FIG. 11 is a cross-sectional front view of a portion of the melt subassembly of FIG. 4, including another embodiment of a level sensor having a different size.

An alternative embodiment of the level sensor 318 is shown mounted within the receiving space 16 of FIG. 11. In this embodiment, the level sensor 318 and the corresponding driven electrode 400 have been reduced in size to provide a larger spacing between the drive electrode 400 and the bottom of the receiving space 16. As previously described, the bottom of the receiving space 16 is located immediately adjacent to the top of the partitions 110 defined by the heater unit 20. It is highly undesirable to permit the level of adhesive to fall below the top of the partitions 110 because the rapid increase of temperature of uncovered portions of these partitions 110 can lead to charring or degradation of new adhesive added to the receiving space 16. Thus, to provide less likelihood that an empty hopper condition sensed by the driven electrode 400 will occur too late to avoid uncovering the heater unit 20, the bottom of the driven electrode 400 is located higher in the receiving space 16 to thereby provide an empty hopper condition or signal earlier (e.g., such as when the receiving space is only 30% filled). In this embodiment, the driven electrode 400 may define a surface area $SA_{PE}$ of about 5.0 square inches and the sidewall 98 of the receiving space 16 may define a surface area $SA_H$ of about 10.7 square inches, such that the level sensor 18 defines a ratio of the surface areas of about 0.468 to 1. This ratio of surface areas or size of the driven electrode 400 is still sufficient to provide the broader sensing window, and it will be understood that the particular ratio or sizes may be modified in other embodiments consistent with the scope of the invention.

With reference to FIGS. 12 through 15, an advantageous control subroutine used to operate the level sensors 18, 318 of the previously described embodiments is shown in detail. In this regard, the measurements of dielectric capacitance performed by the level sensor 18 are affected in a known manner by changes in temperature at the level sensor 18. The level sensor 18 reads that the receiving space 16 is less full than it really is when the temperature of the level sensor 18 drops, and this can lead to an overfill condition if too many refills are actuated using the fill system 52. As a result, to overcome these problems, the measurements may be adjusted according to the known temperature adjustment curve for the level sensor 18, assuming that the temperature of the level sensor 18 is known when the dielectric capacitance measurements are taken.

Figure 14:
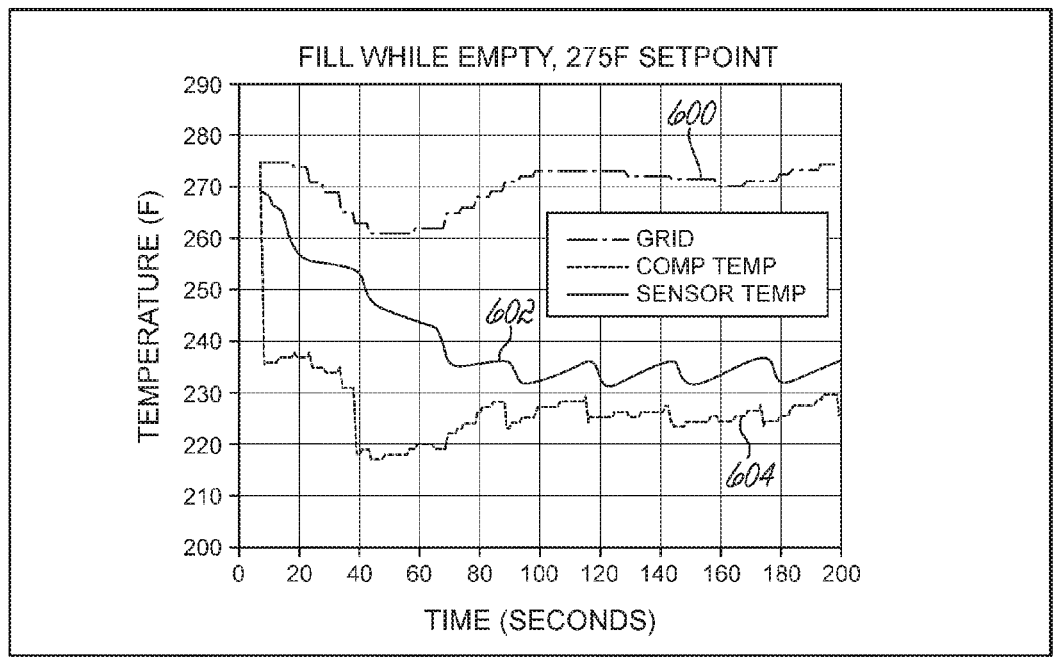
FIG. 14 is a graph showing test results during operation of the series of operations in FIG. 12 and the adhesive dispensing device, thereby showing that the estimated temperature of the level sensor tracks closely to the actual temperature of the level sensor.

One method of estimating this temperature would be to use the temperature readings at the heater unit 20 provided by the corresponding temperature sensor 122, but the "grid temperature" does not closely track the temperature at the level sensor 18, as shown in FIG. 14 and described in further detail below. Another method of obtaining this temperature is to provide an additional temperature sensor at the level sensor 18. However, in order to minimize costs and complexity of the design, the advantageous control subroutine uses the controller 48 and the timer 53 to estimate the temperature changes at the level sensor 18 and adjust the fill level measurements accordingly. As this process is performed entirely in software, there are no additional costs of manufacturing or maintaining the dispensing device 10, but the resulting operation is improved over systems that do not compensate for temperature changes.

Figure 12:
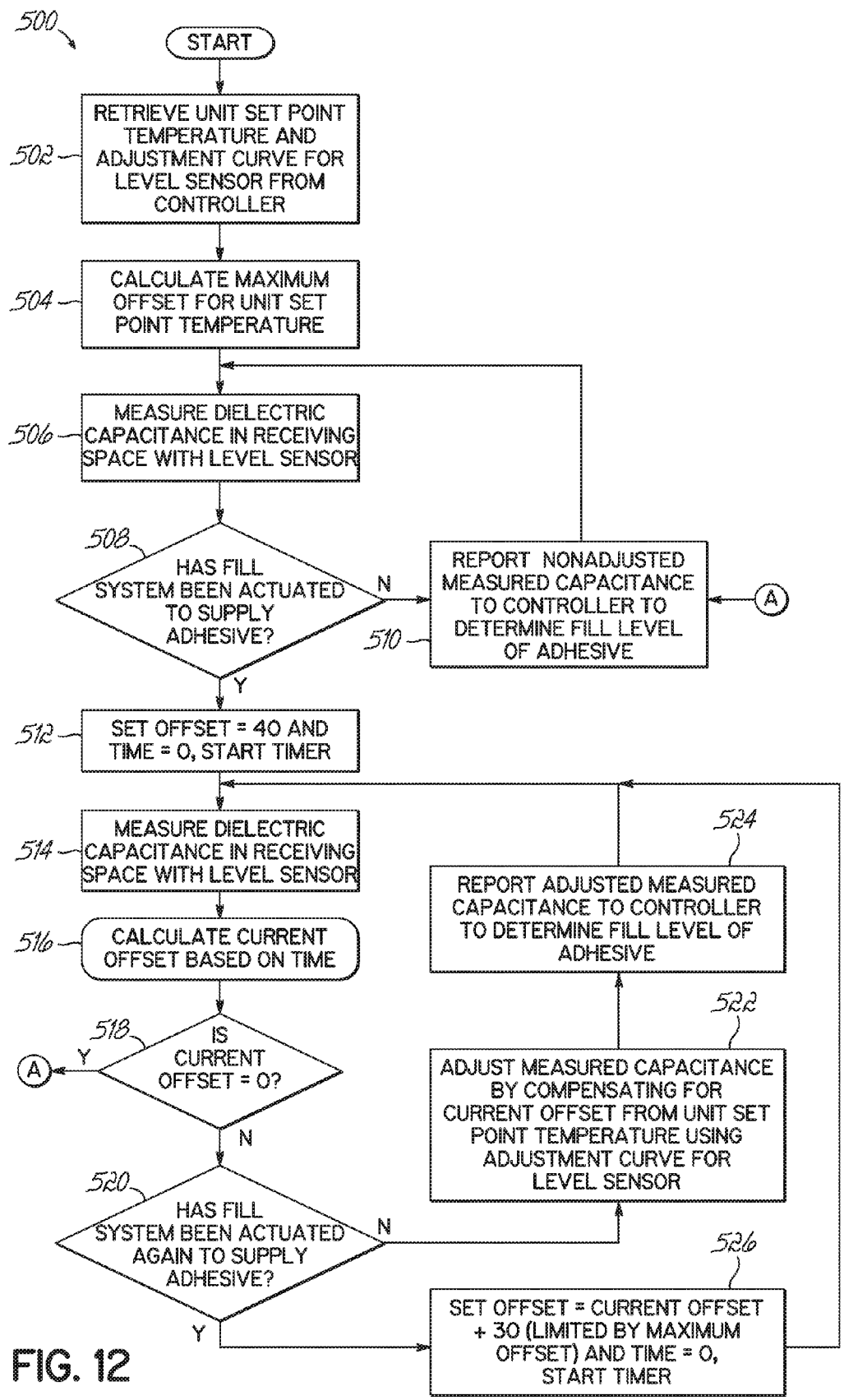
FIG. 12 is a flowchart illustrating a series of operations performed by a controller of the adhesive dispensing devices of FIGS. 1 and 7 to compensate for temperature changes at the level sensor.

Beginning with FIG. 12, a series of operations 500 is provided for compensating the measured dielectric capacitances from the level sensor 18 based on the temperature changes that regularly occur as a result of the cold pressurized air and unmelted adhesive being delivered into the receiving space 16. The controller 48 begins by retrieving the unit set point temperature that the heater unit 20 is set to achieve and an adjustment curve for differing temperatures of the level sensor 18 from memory (block 502). These elements are known and pre-programmed into the memory of the controller 48. The controller 48 also calculates a maximum offset that is allowed to be applied to the estimated temperature of the level sensor 18 (block 504). This maximum offset is a function of the unit set point temperature and describes the lowest temperature that the level sensor 18 will drop to during normal operation of the heater unit 20 and the dispensing device 10. For example, the maximum offset may be calculated by the following formula: (0.35)*(Unit Set Point Temperature)−37.5° F. A set value or a different formula may be used in alternative embodiments, but this formula is believed to accurately reflect that the maximum temperature drop is a function of the unit set point temperature.

Assuming that the dispensing device 10 is in a steady state at this juncture (e.g., the offset to be applied to the temperature at the level sensor 18 would be zero), the level sensor 18 then measures the dielectric capacitance of the air and adhesive within the receiving space 16 as described in detail above (block 506). The controller 48 determines whether the fill system 52 has been actuated to supply adhesive to the receiving space 16 (block 508). If a supply has not been actuated, then the control subroutine reports a non-adjusted measured capacitance from the level sensor 18 to the controller 48 for the determination of the fill level of adhesive (block 510). In this regard, when the offset is equal to zero and the level sensor 18 is operating at steady state conditions, there is no need to compensate for a temperature change. The control subroutine then returns to step 506 to measure the dielectric capacitance again, thereby updating the controller 48 on any changes in fill level within the receiving space 16.

Whenever it is determined that the fill system 52 has been actuated to refill the receiving space 16, the control subroutine moves instead to set an "offset" variable equal to 40° F. and a "time" variable equal to zero (block 512). The controller 48 actuates the timer 53 to begin tracking the time variable since this most recent refill occurred. Then, similar to the steps above, the level sensor 18 measures the dielectric capacitance of the air and adhesive within the receiving space 16 (block 514). The controller 48 then calculates a current offset for this measurement of the dielectric capacitance (block 516), and this process is described in further detail with reference to FIG. 13 below. The current offset is the amount of estimated temperature change from the unit set point temperature that is applied at any given time to adjust the capacitance readings from the level sensor 18. Once this current offset is calculated, the controller 48 determines if the current offset is equal to zero (block 518), which would indicate that the level sensor 18 should be back up to the steady state temperature. If the current offset is equal to zero, then the control subroutine returns to step 510 to report a non-adjusted measured capacitance to the controller 48 so that the fill level of adhesive can be determined from this measured capacitance. To this end, anytime the current offset reaches zero, the process of using the non-adjusted measured capacitances begins again until the fill system 52 is actuated once more, thereby bringing more cold air and adhesive into the receiving space 16.

If the current offset is a non-zero value at step 518, which implies that the level sensor 18 has likely not returned to the steady state temperature. As a result, the control subroutine continues by determining if the fill system 52 has been actuated again to supply more adhesive to the receiving space 16 (block 520). If such a refill has not occurred, then the control subroutine adjusts the measured capacitance by compensating for the change in temperature of the level sensor 18, which is the current offset (block 522). This adjustment is performed using the known temperature adjustment curve for the level sensor 18, which is predetermined for each level sensor 18 as described above. In an exemplary embodiment, this adjustment may be performed using the formula:

$$\text{Capacitance(Farads)} = -1.04939E\text{-}17*(\text{Sensor Temperature})^2 + 9.32678E\text{-}15*(\text{Sensor Temperature}) + 1.176989E\text{-}10.$$

This adjusted measured capacitance is then reported to the controller 48 for use in determining the fill level of the adhesive in the receiving space 16 (block 524). Accordingly, the fill level of the adhesive is more accurately determined because a more accurate estimation of temperature at the level sensor 18 is used. The differences obtained from using this adjustment are described with reference to the graph in FIG. 15 below. The control subroutine then returns to block 514 to measure the dielectric capacitance once again to update the fill level for the controller 48.

At block 520, if the fill system 52 has been actuated again to refill the receiving space 16, but the current offset is not equal to zero, then the offset variable must be increased once again. Rather than increasing the offset by 40° F. as was done at block 512 when the current offset was zero, the control subroutine instead sets the offset variable equal to the current offset plus an additional 30° F. (block 526), but this offset variable cannot be set larger than the maximum offset that was calculated in block 504. Also at block 526, the elapsed time variable is reset to zero because a new refill has occurred, and the timer 53 is started anew. The control subroutine then returns to block 514 to being the process again by measuring the dielectric capacitance at the level sensor 18 again. The changes in offset (40° F. and 30° F.) used during these various states have been determined using the test results below and are a good general approximation of how much the level sensor 18 drops in temperature during a refill event. To this end, in the exemplary embodiment shown, test results indicated that when the level sensor 18 was operating at steady state temperature conditions, the drop in temperature was about 40° F., while when the level sensor 18 was cooler and still recovering from a previous drop in temperature, the added drop in temperature caused by the refill was about 30° F. in addition. Thus, it is possible, when adhesive supply happens frequently, to have the offset accumulate all the way to the maximum offset described above. It will be understood that different threshold offset values may be provided in other embodiments of the level sensor 18. In summary, the control subroutine shown in FIG. 12 allows the measured capacitance at the level sensor 18 to be adjusted when such adjustment is appropriate in view of likely cooling caused by recent supplies of cold adhesive and air from the fill system 52 into the receiving space 16. Advantageously, this adjustment is done without additional equipment in the dispensing device 10.

Figure 13:
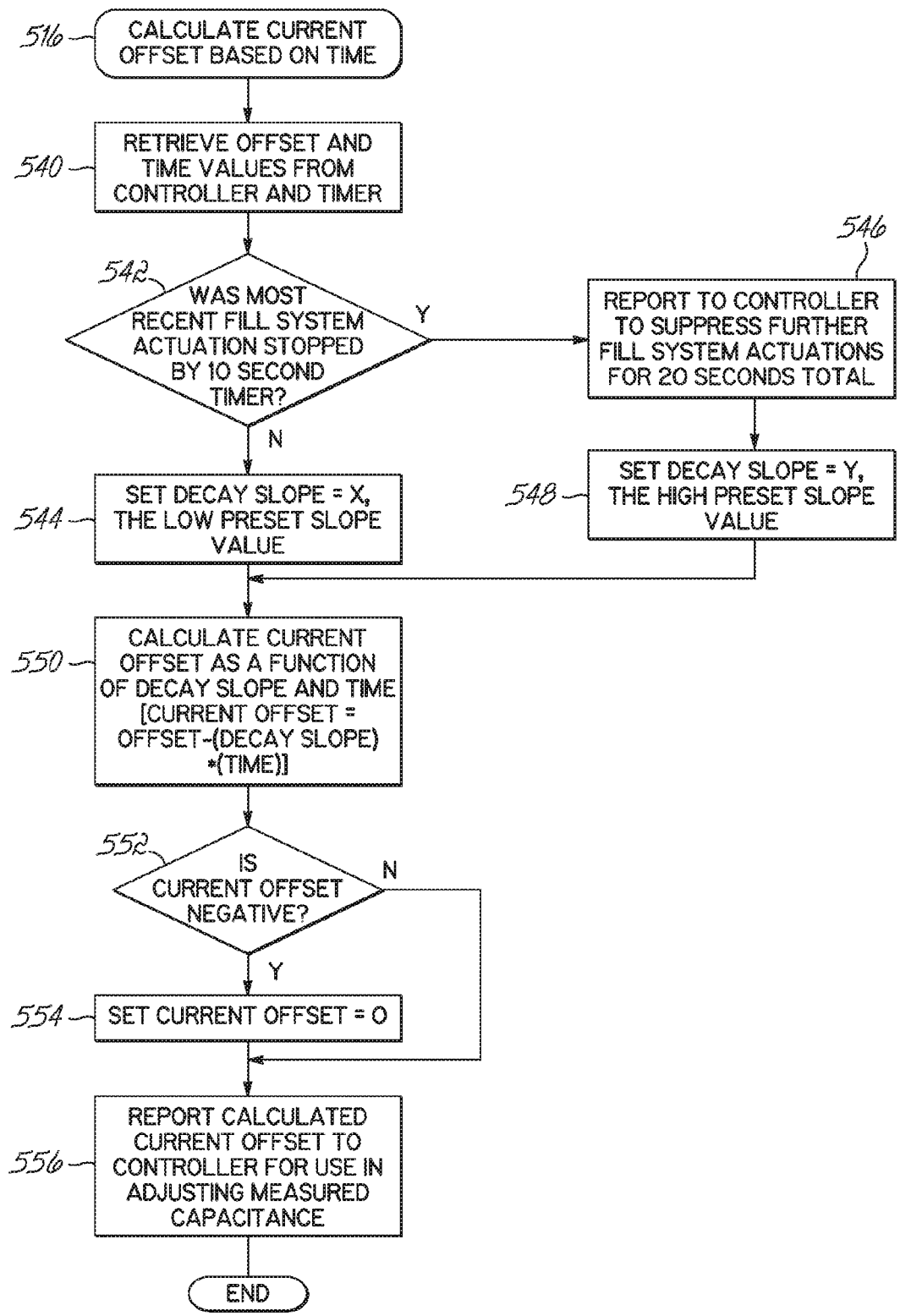
FIG. 13 is a flowchart illustrating a series of operations performed by the controller to calculate a current offset for the level sensor based on time, which is a function within the series of operations shown in FIG. 12.

Now turning to FIG. 13, the process for calculating the current offset based on elapsed time is shown as a series of operations 516. This series of operations begins by retrieving the offset variable and the time variable from the controller 48 (and the timer 53, if applicable) (block 540). When actuating the fill system 52 of the exemplary embodiment, the refilling process may be stopped in one of two ways: when the level sensor 18 determines that the adhesive has reached a full threshold in the receiving space 16, or when a maximum threshold refill time has been exceeded. This maximum threshold refill time is set to be 10 seconds in the exemplary embodiment, but this maximum threshold may be modified for dispensing devices 10 of other embodiments, including differently-shaped or sized receiving spaces 16. Thus, after retrieving the offset and time variables, the controller 48 determines if the most recent fill system actuation was stopped by the 10 second timer (block 542), as this would indicate that the receiving space 16 received a maximum allowed amount of cold air and adhesive in the most recent supply actuation.

If the controller 48 determines that the fill system actuation was not stopped by the 10 second timer, the controller 48 sets a decay slope variable equal to a first preset slope value (which is 0.12° F. per second in the exemplary embodiment) (block 544). If the most recent fill system actuation was stopped by the timer, then the controller 48 is notified to suppress further fill system actuations for a period of time such as 20 seconds (block 546), so as to limit the frequency with which the fill system 52 is actuated. The controller 48 then sets the decay slope variable equal to a second preset slope value that is higher than the first preset slope value (and which is 0.2° F. per second in the exemplary embodiment) (block 548). The higher decay slope value is used when the refill operation times out because the receiving space 16 and the level sensor 18 are likely not fully covered with adhesive and therefore are more likely to more quickly recover temperature loss caused by the supply of adhesive and air into the receiving space 16.

Regardless of whichever slope value is assigned to be the decay slope, the controller 48 then proceeds to calculate the current offset at a function of the decay slope and the elapsed time since the most recent actuation of the fill system 52 (block 550). In the exemplary embodiment, this function is a linear function defined by the following formula:

(Current Offset)=Offset−(Decay Slope)*(Time).

Once this current offset is calculated, the controller 48 determines if the calculated value is negative (block 552), and if so, the current offset is set to zero (block 554) because the time elapsed is deemed to be sufficient for the level sensor 18 to return to the steady state temperature. If the current offset is not negative, or after the current offset is set to zero at block 554, the controller 48 receives the calculated current offset so that it may be used in the adjustment of the measured capacitance as described above in the series of operations 500 shown in FIG. 12.

Figure 15:
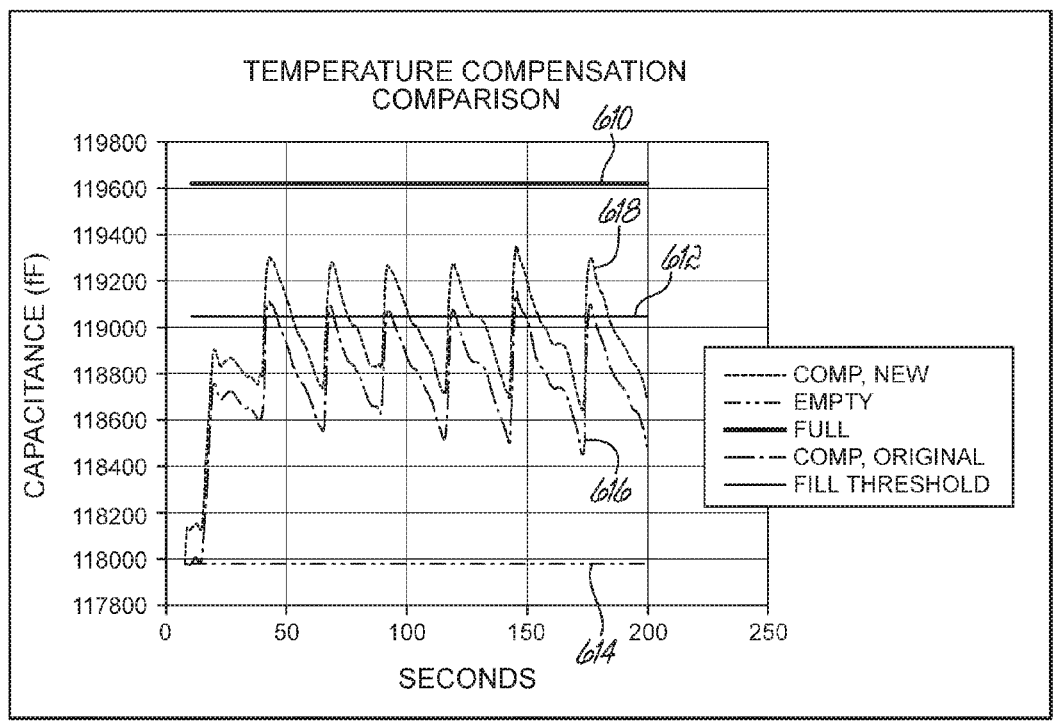
FIG. 15 is a graph showing test results during operation of the level sensor according to the series of operations in FIG. 12, with a comparison of the capacitance measurements of the level sensor when the series of operations in FIG. 12 is not used.

The operation and advantages of these series of operations are further made clear in the graphs of FIGS. 14 and 15. FIG. 14 illustrates test results for the temperature of various elements of the adhesive dispensing device 10 over a period of about 200 seconds. After an initial filling and reheating period shown from about 0 seconds to about 100 seconds, the differences in the temperature of the heater unit 20 (shown by trend line 600) and the actual temperature of the level sensor 18 (shown by trend line 602) is a significant difference as shown. This explains why using the temperature from the temperature sensor 122 at the heater unit 20 is not a good method for estimating the temperature of the level sensor 18. The estimated or computed temperature of the level sensor 18 over the same time period when using the compensation method described above in FIGS. 12 and 13 is shown at trend line 604. As shown in FIG. 14, this trend line 604 follows the actual sensor temperature of trend line 602 far more closely than the heater unit 20 or "grid" temperature. The estimated or compensated temperature from the software/controller 48 is slightly less than the actual temperature of the level sensor 18, but this is acceptable because using a lower temperature results in the receiving space 16 being refilled slightly in advance of when the fill level actually reaches a refill threshold. This is a better result than refilling after the fill level has dropped below the refill threshold because such an arrangement could potentially lead to uncovering of the heater unit 20. Consequently, even without using a separate temperature sensor at the level sensor 18, the temperature of the level sensor 18 during operation can be sufficiently estimated for accurately adjusting the dielectric capacitance readings from the level sensor 18 during operation.

The results of the compensation method described above are more clearly revealed in the graph of FIG. 15, which is a comparison of capacitance measurements, both without compensation and with compensation, during the test period shown in FIG. 14. For reference, the capacitance levels indicating the full condition (trend line 610), the refill threshold (trend line 612), and the empty condition (trend line 614) are shown in addition to the capacitance measurements from the test results. As shown near the time 0 seconds on the graph, the receiving device 16 began the test in a substantially empty state. Consequently, it took a couple of refill cycles by the fill system 52 to get the fill level of adhesive over the refill threshold shown by trend line 612. From about time 50 seconds onward, the substantially constant pumping of adhesive out of the dispensing device 10 results in a steady decline in sensed fill level followed by an increase when the fill system 52 is actuated to supply more adhesive to the receiving space 16, and then another steady decline of fill level, and so on. The capacitance measurements compensated using the series of operations shown above in FIGS. 12 and 13 are shown by trend line 618, while the non-adjusted capacitance measurements are shown by trend line 616. As shown in FIG. 15, the non-adjusted capacitance measurements barely reach above the refill threshold, although it is known from the compensated capacitance measurements that the actual fill level exceeds the refill threshold by a sizeable margin. Accordingly, if the non-adjusted capacitance values were used in this test, the dispensing device 10 would be more prone to refilling the receiving space 16 too often when a refill was not necessary, thereby leading to overfill and a messy condition that could interfere with future operation of the cyclonic separator unit 14, for example. Therefore, the compensation provided by the control subroutine or series of operations described above corrects for inaccurate readings caused by changing temperatures at the level sensor 18, and problems are avoided without the need for additional sensors or other equipment in the receiving space 16.

Accordingly, the receiving space 16 and the level sensor 18 are optimized to produce highly responsive and accurate readings of the level of adhesive material held by the receiving space 16. Thus, regardless of whether the adhesive dispensing device 10 is operating at a high flow rate or a low flow rate, the controller 48 is provided with sufficient information (via the multiple control signals generated and enabled as a result of the broader sensing window) to keep the level of adhesive material at a desired level within the receiving space 16 and the reservoir 22. To this end, the melt subassembly 12 is prevented from running out of adhesive material or filling up with too much adhesive material. Moreover, the size and positioning of the plate element 96 along the majority of a sidewall 98 of the receiving space 16 enables rapid melting off of any adhesive pellets 160 or residue stuck on the level sensor 18 above the actual level of the adhesive material in the receiving space 16. The broader sensing window defined by the level sensor 18 is therefore less susceptible to localized events or effects as well as more sensitive and responsive to fill level changes within the receiving space 16. Thus, the level sensor 18 advantageously improves the response time and accuracy when detecting levels of material within the receiving space 16.

While the present invention has been illustrated by a description of several embodiments, and while such embodiments have been described in considerable detail, there is no intention to restrict, or in any way limit, the scope of the appended claims to such detail. Additional advantages and modifications will readily appear to those skilled in the art. For example, the level sensor 18 described in connection with the receiving space 16 may be used with other elements of the melt subassembly 12 or other types of material moving systems. Therefore, the invention in its broadest aspects is not limited to the specific details shown and described. The various features disclosed herein may be used in any combination necessary or desired for a particular application. Consequently, departures may be made from the details described herein without departing from the spirit and scope of the claims which follow.

What is claimed is:

1. An adhesive dispensing device, comprising:
a melt subassembly including a heater unit adapted to melt and heat an adhesive, a receiving space positioned to receive unmelted adhesive and deliver the adhesive into said heater unit, a reservoir for receiving the adhesive from said heater unit, and a pump for directing the adhesive from said reservoir to an outlet, said receiving space and reservoir defining a collective storage volume and said heater unit defining a surface area in contact with the adhesive; and a control subassembly including a controller configured to operate said pump and said heater unit to dispense adhesive through said outlet, a relation of the collective storage volume of said receiving space and said reservoir to the surface area of said heater unit being less than 1 cubic inch of volume to 1 square inch of surface area.

2. The adhesive dispensing device of claim 1, wherein the relation of the collective storage volume to the surface area of said heater unit is about 0.7 cubic inches of volume to 1 square inch of surface area.

3. The adhesive dispensing device of claim 1, wherein said control subassembly is adapted to actuate supply of unmelted adhesive to said receiving space as melted adhesive is pumped from said reservoir, and wherein the unmelted adhesive delivered to said receiving space defines a round pellet shape that is configured to be melted at the heater unit.

4. The adhesive dispensing device of claim 3, wherein said receiving space is at least partially defined by a sidewall, and a level sensor having an electrically driven electrode is mounted along said sidewall such that a fill level of adhesive in said receiving space is detected by a change in dielectric capacitance from said electrically driven electrode to a ground at least partially defined at said sidewall.

5. The adhesive dispensing device of claim 3, wherein said melt subassembly further comprises:

a cyclonic separator unit configured to receive pellets of adhesive in an air flow and reduce the velocity of the air flow and the pellets of adhesive before depositing the pellets of adhesive into said receiving space.

6. The adhesive dispensing device of claim 1, wherein the reservoir defines an open top end and a bottom end opposite the open top end, wherein the reservoir is operatively coupled to said heater unit, the pump is located at least partially within a heated housing, and said heated housing heats said pump and adhesive within said pump during startup and regular operation of the adhesive dispensing device, the melt subassembly further including a manifold in fluid communication with said reservoir and said pump, said manifold including at least one conduit that extends from the bottom end of the reservoir to the pump, wherein the conduit is configured to deliver adhesive from the reservoir to the pump, and said pump is in fluid communication with said reservoir to receive the heated and melted adhesive from said reservoir through the conduit.

7. The adhesive dispensing device of claim 6, wherein said manifold includes at least one outlet configured to receive adhesive that is removed from said reservoir by said pump.

8. The adhesive dispensing device of claim 7, wherein said manifold defines said heated housing such that said manifold at least partially surrounds said pump and supplies heat energy to said pump.

9. The adhesive dispensing device of claim 8, wherein said reservoir directly abuts said manifold so that said reservoir provides heat energy by conduction into said manifold for heating said pump.

10. The adhesive dispensing device of claim 9, wherein said manifold is integrally formed as a unitary piece with said reservoir, thereby enabling the conduction of heat energy from said reservoir to said manifold and said pump.

11. The adhesive dispensing device of claim 8, wherein the melt subassembly further comprises an insulating external housing at least partially surrounding said heater unit, said reservoir, and said manifold collectively in order to encourage conduction of heat energy to said pump.

12. The adhesive dispensing device of claim 1, wherein the receiving space is defined by at least one sidewall and a top wall having an inlet aperture and the reservoir defines an open top end and a bottom end opposite the open top end, the melt subassembly further compromising:

a fluid level sensor for measuring a fill level of the adhesive within said receiving space to determine when said receiving space needs to be refilled with adhesive; and a manifold defining a conduit that extends from the bottom end of the reservoir to the pump, wherein the conduit is configured to deliver adhesive from the reservoir to the pump, said receiving space, said heater unit, said reservoir, and said manifold are positioned above and/or below one another in a common vertical plane, and said pump is vertically-oriented and is centered along another vertical plane spaced from and parallel to the common vertical plane.

13. The adhesive dispensing device of claim 12, further comprising a cyclonic separator unit coupled to said receiving space, said cyclonic separator unit including an elongate pipe including a top end and a bottom end, said top end communicating with a tangential inlet pipe such that a flow of air and adhesive pellets flows from said tangential inlet pipe to spiral downwardly in said elongate pipe toward said bottom end and said inlet aperture of said receiving space, thereby decelerating the adhesive pellets before delivery into said receiving space.

14. The adhesive dispensing device of claim 1, wherein said pump is located at least partially within a heated housing, wherein said heated housing heats said pump and adhesive within said pump during startup and regular operation of the melt subassembly.

15. The adhesive dispensing device of claim 12, wherein said pump is located at least partially within a heated housing, wherein said heated housing heats said pump and adhesive within said pump during startup and regular operation of the heater unit.

16. The adhesive dispensing device of claim 1, wherein the collective storage volume of said receiving space and said reservoir is less than 2 liters.

\* \* \* \* \*